US012780944B2

(12) United States Patent
Yang et al.

(10) Patent No.: US 12,780,944 B2
(45) Date of Patent: Nov. 3, 2026

(54) ANTI-MASP2 ANTIBODY, ANTIGEN-BINDING FRAGMENT THEREOF AND MEDICAL USE THEREOF

(71) Applicants: JIANGSU HENGRUI PHARMACEUTICALS CO., LTD., Lianyungang (CN); SHANGHAI SHENGDI PHARMACEUTICAL CO., LTD., Shanghai (CN)

(72) Inventors: Xiaofeng Yang, Lianyungang (CN); Jing Wen, Lianyungang (CN); Jingyang Zhang, Lianyungang (CN); Caihong Zhou, Shanghai (CN); Cheng Liao, Shanghai (CN)

(73) Assignees: JIANGSU HENGRUI PHARMACEUTICALS CO., LTD., Lianyungang (CN); SHANGHAI SHENGDI PHARMACEUTICAL CO., LTD., Shanghai (CN)

( * ) Notice: Subject to any disclaimer, the term of this patent is extended or adjusted under 35 U.S.C. 154(b) by 549 days.

(21) Appl. No.: 18/288,078

(22) PCT Filed: Apr. 25, 2022

(86) PCT No.: PCT/CN2022/088914
§ 371 (c)(1),
(2) Date: Oct. 24, 2023

(87) PCT Pub. No.: WO2022/228364
PCT Pub. Date: Nov. 3, 2022

(65) Prior Publication Data

US 2024/0209114 A1 Jun. 27, 2024

(30) Foreign Application Priority Data

Apr. 25, 2021 (CN) ........................ 202110450267.0

(51) Int. Cl.
*C07K 16/40* (2006.01)
*A61K 39/00* (2006.01)
*A61P 9/10* (2006.01)

(52) U.S. Cl.
CPC ................ *C07K 16/40* (2013.01); *A61P 9/10* (2018.01); *A61K 39/00* (2013.01); *A61K 2039/505* (2013.01); *C07K 2317/20* (2013.01); *C07K 2317/21* (2013.01); *C07K 2317/24* (2013.01); *C07K 2317/94* (2013.01)

(58) Field of Classification Search
CPC ............... C07K 16/40; C07K 2317/20; C07K 2317/21; C07K 2317/24; C07K 2317/94; C07K 2317/33; C07K 2317/76; C07K 2317/92; A61P 9/10; A61P 7/00; A61P 9/00; A61K 39/00; A61K 2039/505
See application file for complete search history.

(56) References Cited

U.S. PATENT DOCUMENTS

| | | | |
|---|---|---|---|
| 2006/0002937 | A1 | 1/2006 | Schwaeble et al. |
| 2006/0140939 | A1 | 6/2006 | Fung |
| 2009/0017031 | A1 | 1/2009 | Fung |
| 2012/0258095 | A1 | 10/2012 | Demopulos et al. |
| 2015/0239985 | A1 | 8/2015 | Demopulos et al. |
| 2017/0166658 | A1 | 6/2017 | Demopulos et al. |
| 2019/0292272 | A1 | 9/2019 | Demopulos et al. |
| 2022/0089781 | A1 | 3/2022 | Demopulos et al. |

OTHER PUBLICATIONS

S. Elhadad et al., MASP2 levels are elevated in thrombotic microangiopathies: association with microvascular endothelial cell injury and suppression by anti-MASP2 antibody narsoplimab, Clinincal & Experimental Immunology, Jan. 2021, vol. 203, No. 1, pp. 96-104. doi: 10.1111/cei.13497.

*Primary Examiner* — Alana Harris Dent
(74) *Attorney, Agent, or Firm* — Morgan, Lewis & Bockius LLP

(57) ABSTRACT

An anti-MASP2 antibody, an antigen-binding fragment thereof and the medical use thereof. Specifically, provided are an anti-MASP2 antibody or an antigen-binding fragment thereof, a pharmaceutical composition thereof, a method for treating diseases such as IgA nephropathy and a related pharmaceutical use.

17 Claims, 6 Drawing Sheets

Specification includes a Sequence Listing.

ANTI-MASP2 ANTIBODY, ANTIGEN-BINDING FRAGMENT THEREOF AND MEDICAL USE THEREOF

CROSS-REFERENCE TO RELATED APPLICATIONS

The present application is a national stage application of International Patent Application No. PCT/CN2022/088914, filed Apr. 25, 2022, which claims the benefit of and priority to Chinese Patent Application No. CN202110450267.0 filed on Apr. 25, 2021, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 23, 2023, is named "722037CPUS 126268-5067-US Sequence Listing.txt" and is approximately 79,072 bytes in size.

TECHNICAL FIELD

The present disclosure relates to the field of biological pharmaceutics, and in particular to an anti-MASP2 antibody and an antigen-binding fragment thereof, a pharmaceutical composition thereof, and related pharmaceutical use.

BACKGROUND

The complement system is a protein present in the serum, interstitial fluid, and cell membrane surface of humans and animals. It is biologically active after activation and can mediate immune and inflammatory responses. The complement system consists of nearly 40 components, mostly glycoproteins, including C1q, C1r, C1s, C2-C9, factor D and factor B, as well as 10 regulatory proteins and 10 complement receptors. Complement is widely involved in the body's microbial defense response and immune regulation, and also in the injurious effects of immunopathology. Complement is an important effector system and effector amplification system of innate immunity.

The activation process of the complement system is manifested as a serine protease cascade enzymatic reaction, which is divided into three types: a classic pathway, an alternative pathway, and a lectin pathway, ultimately mediating the activation of the terminal pathway marked by the formation of a membrane attack complex. In healthy people, the alternative pathway remains activated at a low level for a long period of time to monitor pathogenic microbial invasion. Healthy cells also inhibit the attack of the complement system by expressing complement regulatory proteins such as CD55 and CD59. Three pathways are generally activated on the surface of apoptotic cells or microorganisms. The classic pathway is that after an immune complex formed by the binding of an antibody (IgG1, IGG, IgG3, IgG4, or IgM) to an antigen is recognized by C1q, C1s and C1r, C2 and C4 are activated to form C4bC2a (i.e., C3 convertase), and finally the formation of a membrane attack complex consisting of C5-C9 is promoted. The alternative pathway is an activation pathway directly starting from spontaneous hydrolysis of C3, and under the stimulation of activating substances such as bacterial cell wall components LPS, polysaccharides such as zymosan, peptidoglycans, and teichoic acid, factor D hydrolyzes C3-binding factor B to form C3bBb3, and then the chain reaction of the components C5 to C9 is completed. In the lectin pathway, mannose, N-acetylmannose, N-acetylglucosamine, fucose, and the like, on the surfaces of various pathogenic microorganisms are directly recognized as carbohydrate structures with terminal glycosyl groups by mannan-binding lectin (MBL) or ficolin (FCN) in plasma, and then the classic complement pathway is activated.

Clinical trials and research evidence show that abnormal activation of the complement system is associated with acute sepsis, ischemia reperfusion-related stroke, myocardial infarction, or graft rejection, and is associated with the occurrence of chronic autoimmune diseases such as arthritis, age-related macular degeneration, microvascular thrombosis, chronic kidney diseases, or hemolytic diseases. Among the current investigational drugs targeting complement, a C5 antibody eculizumab was approved for marketing in 2007, mainly for the treatment of hemolytic diseases PNH and aHUS, myasthenia gravis, and other diseases. Other MASP2 antibodies targeting the lectin pathway and drugs targeting factor D, factor B, and C3 of the alternative pathway are also in clinical phases II to III. In terms of safety, targeting the complement system, overall, is safe and tolerable. Given that the complement system is involved in the regulation of B cell development and T cell activation, complement factor gene-deficient mice are defective in reproductive ability or embryonic development and have an increased risk of infection. Therefore, the development of a drug for a specific upstream target of the complement pathway can reduce side effects after overall inhibition of the complement pathway while maintaining efficacy.

The MASP2 protein is a core hydrolase of the lectin pathway, and consists of CUB and EGF domains responsible for binding to MBL at the N-terminus, a CCP domain binding to downstream substrates C4 and C2, and an enzymatic domain SP at the C-terminus. The MBL-MASP complex binds to a carbohydrate structure on the surface of pathogens, resulting in the independent activation of MASP-1 and MASP-2. Activated MASP2 exerts its SP activity to cleave C4 and C2 to form a C3 convertase C4b2a, and is ultimately able to activate the lectin pathway-mediated complement system, which has been shown to be associated with IgA nephropathy, stroke, and myocardial ischemia. In mouse models of MCAO cerebral stroke and acute myocardial infarction, the MASP2 deletion can be seen to significantly reduce the infarct size. MBL-MASP2 mainly recognizes galactose modification-deficient IgA on mesangium, and the activation of the LP pathway promotes cytokine secretion, which ultimately causes damage to tubular epithelial cells and podocytes, and abnormal function of the kidney.

The MASP2 monoclonal antibody narsoplimab (OMS721) from Omeros was developed primarily by inhibiting lectin-mediated complement system activation for treating a variety of inflammatory-related diseases, including thrombotic microangiopathy (TMA), IgA nephropathy, hemolytic uremic syndrome (HUS), lupus nephritis, membranous glomerulonephritis, glomerulonephritis, age-related macular degeneration, reperfusion injury, myocardial infarction, diabetic neuropathy, stroke, and graft-versus-host disease. The study of narsoplimab for TMA is in pre-registration status in the U.S., the study of narsoplimab for HUS and IgA nephropathy is in clinical phase III, and the study of narsoplimab for lupus nephritis, membranous glomerulonephritis, and glomerulonephritis is in clinical phase II.

In view of the important role of MASP2 in the lectin pathway, it is still an urgent problem in the prior art to provide an anti-MASP2 antibody with a novel structure for inhibiting MASP2-dependent complement activation and treating diseases caused by complement system abnormalities.

SUMMARY

The present disclosure provides an anti-MASP2 antibody and an antigen-binding fragment thereof, a nucleic acid encoding the same, a vector comprising the nucleic acid, a host cell, a pharmaceutical composition comprising the anti-MASP2 antibody and the antigen-binding fragment thereof, a method thereof for treating or delaying a complement system-related disease, and use thereof.

Anti-MASP2 Antibody and Antigen-Binding Fragment Thereof

The present disclosure provides an anti-MASP2 antibody and an antigen-binding fragment thereof, which comprise a heavy chain variable region (VH) and a light chain variable region (VL), wherein:

1) the VH comprises a HCDR1, a HCDR2, and a HCDR3 in a VH set forth in any one of SEQ ID NOs: 7, 9, and 11, and/or, the VL comprises a LCDR1, a LCDR2, and a LCDR3 in a VL set forth in any one of SEQ ID NOs: 8, 10, and 12;
2) the VH comprises a HCDR1, a HCDR2, and a HCDR3 in a VH set forth in SEQ ID NO: 13, and/or, the VL comprises a LCDR1, a LCDR2, and a LCDR3 in a VL set forth in SEQ ID NO: 14; or
3) the VH comprises a HCDR1, a HCDR2, and a HCDR3 in a VH set forth in SEQ ID NO: 15, and/or, the VL comprises a LCDR1, a LCDR2, and a LCDR3 in a VL set forth in SEQ ID NO: 16;

the HCDR1, HCDR2, HCDR3, LCDR1, LCDR2, and LCDR3 of the VH and VL are defined according to the Kabat, IMGT, Chothia, AbM, or Contact numbering scheme, and in some embodiments, according to the Kabat numbering scheme.

In some embodiments, provided are the anti-MASP2 antibody and the antigen-binding fragment thereof, wherein, 1-1) the VH comprises a HCDR1, a HCDR2, and a HCDR3 in a VH set forth in SEQ ID NO: 7, and/or, the VL comprises a LCDR1, a LCDR2, and a LCDR3 in a VL set forth in SEQ ID NO: 8;
1-2) the VH comprises a HCDR1, a HCDR2, and a HCDR3 in a VH set forth in SEQ ID NO: 9, and/or, the VL comprises a LCDR1, a LCDR2, and a LCDR3 in a VL set forth in SEQ ID NO: 10;
1-3) the VH comprises a HCDR1, a HCDR2, and a HCDR3 in a VH set forth in SEQ ID NO: 11, and/or, the VL comprises a LCDR1, a LCDR2, and a LCDR3 in a VL set forth in SEQ ID NO: 12.

The present disclosure provides an anti-MASP2 antibody and an antigen-binding fragment thereof, which comprise a heavy chain variable region (VH) and a light chain variable region (VL), wherein:

1) the VH comprises a HCDR1, a HCDR2, and a HCDR3 set forth in SEQ ID NOs: 17, 18, and 26, respectively, and/or, the VL comprises a LCDR1, a LCDR2, and a LCDR3 set forth in SEQ ID NOs: 20, 27, and 22, respectively;

wherein, SEQ ID NO: 17 has a sequence of SDYAWN:
SEQ ID NO: 18 has a sequence of YISYSGRTSYNPSLKS;
SEQ ID NO: 26 has a sequence of LYA$X_1X_2X_3$, wherein, $X_1$ is selected from the group consisting of L and M, $X_2$ is selected from the group consisting of D and N, and $X_3$ is selected from the group consisting of Y and F;
SEQ ID NO: 20 has a sequence of KASQNVDTNVA;
SEQ ID NO: 27 has a sequence of SASYR$X_4$S, wherein, $X_4$ is selected from the group consisting of Y and F;
SEQ ID NO: 22 has a sequence of QQYNSNPLT:

2) the VH comprises a HCDR1, a HCDR2, and a HCDR3 set forth in SEQ ID NOs: 28, 29, and 30, respectively, and/or, the VL comprises a LCDR1, a LCDR2, and a LCDR3 set forth in SEQ ID NOs: 31, 32, and 33, respectively; or
3) the VH comprises a HCDR1, a HCDR2, and a HCDR3 set forth in SEQ ID NOs: 34, 35, and 36, respectively, and/or, the VL comprises a LCDR1, a LCDR2, and a LCDR3 set forth in SEQ ID NOs: 37, 38, and 39, respectively.

In some embodiments, provided are the anti-MASP2 antibody and the antigen-binding fragment thereof, wherein, the VH comprises a HCDR1, a HCDR2, and a HCDR3 set forth in SEQ ID NOs: 17, 18, and 19, respectively, and/or, the VL comprises a LCDR1, a LCDR2, and a LCDR3 set forth in SEQ ID NOs: 20, 21, and 22, respectively:

the VH comprises a HCDR1, a HCDR2, and a HCDR3 set forth in SEQ ID NOs: 17, 18, and 23, respectively, and/or, the VL comprises a LCDR1, a LCDR2, and a LCDR3 set forth in SEQ ID NOs: 20, 24, and 22, respectively; or the VH comprises a HCDR1, a HCDR2, and a HCDR3 set forth in SEQ ID NOs: 17, 18, and 25, respectively, and/or, the VL comprises a LCDR1, a LCDR2, and a LCDR3 set forth in SEQ ID NOs: 20, 21, and 22, respectively.

In some embodiments, provided is a variant of the anti-MASP2 antibody and the antigen-binding fragment thereof described above, wherein, the VH comprises a HCDR1 having at most 3, 2, or 1 amino acid change compared to SEQ ID NO: 17, a HCDR2 having at most 3, 2, or 1 amino acid change compared to SEQ ID NO: 18, and a HCDR3 having at most 3, 2, or 1 amino acid change compared to SEQ ID NO: 19 or 25; and/or, the VL comprises a LCDR1 having at most 3, 2, or 1 amino acid change compared to SEQ ID NO: 20, a LCDR2 having at most 3, 2, or 1 amino acid change compared to SEQ ID NO: 21, and a LCDR3 having at most 3, 2, or 1 amino acid change compared to SEQ ID NO: 22;

the VH comprises a HCDR1 having at most 3, 2, or 1 amino acid change compared to SEQ ID NO: 17, a HCDR2 having at most 3, 2, or 1 amino acid change compared to SEQ ID NO: 18, and a HCDR3 having at most 3, 2, or 1 amino acid change compared to SEQ ID NO: 23; and/or, the VL comprises a LCDR1 having at most 3, 2, or 1 amino acid change compared to SEQ ID NO: 20, a LCDR2 having at most 3, 2, or 1 amino acid change compared to SEQ ID NO: 24, and a LCDR3 having at most 3, 2, or 1 amino acid change compared to SEQ ID NO: 22;

the VH comprises a HCDR1 having at most 3, 2, or 1 amino acid change compared to SEQ ID NO: 28, a HCDR2 having at most 3, 2, or 1 amino acid change compared to SEQ ID NO: 29, and a HCDR3 having at most 3, 2, or 1 amino acid change compared to SEQ ID NO: 30; and/or, the VL comprises a LCDR1 having at most 3, 2, or 1 amino acid change compared to SEQ ID NO: 31, a LCDR2 having at most 3, 2, or 1 amino acid change compared to SEQ ID NO: 32, and a LCDR3 having at most 3, 2, or 1 amino acid change compared to SEQ ID NO: 33;

the VH comprises a HCDR1 having at most 3, 2, or 1 amino acid change compared to SEQ ID NO: 34, a HCDR2 having at most 3, 2, or 1 amino acid change compared to SEQ ID NO: 35, and a HCDR3 having at most 3, 2, or 1 amino acid change compared to SEQ ID NO: 36; and/or, the VL comprises a LCDR1 having at most 3, 2, or 1 amino acid change compared to SEQ ID NO: 37, and a LCDR2 having at most 3, 2, or 1 amino acid change compared to SEQ ID NO: 38, and a LCDR3 having at most 3, 2, or 1 amino acid change compared to SEQ ID NO: 39.

In some embodiments, the above amino acid changes may be conservative replacements, substitutions or modifications, and/or deletions or additions that do not affect function.

In some embodiments, provided are an anti-MASP2 antibody and an antigen-binding fragment thereof, which comprises at least one or more of any CDR, for example, one or more of any HCDR1 or any HCDR2 or HCDR3 of the present disclosure, and for example, one or more of any LCDR1 or any LCDR2 or LCDR3 of the present disclosure.

In some embodiments, the anti-MASP2 antibody or the antigen-binding fragment thereof of the present disclosure described above is a murine antibody, a chimeric antibody, a humanized antibody or a fully human antibody or a fragment thereof.

In some embodiments, the humanized antibody or the antigen-binding fragment thereof of the present disclosure described above comprises a heavy chain framework region derived from IGKV3-21*01 or IGKV4-30-4*01 and/or a light chain framework region derived from IGKV1-33*01 or IGKV1-27*01.

In some embodiments, provided is the anti-MASP2 antibody or the antigen-binding fragment thereof, wherein, the VH comprises an amino acid sequence set forth in any one of SEQ ID NOs: 7, 9, 11, 47, 48, 49, and 50, and/or, the VL comprises an amino acid sequence set forth in any one of SEQ ID NOs: 8, 10, 12, 51, and 52;

the VH comprises an amino acid sequence set forth in any one of SEQ ID NOs: 13, 42, 43, and 44, and/or, the VL comprises an amino acid sequence set forth in any one of SEQ ID NOs: 14, 45, and 46; or the VH comprises an amino acid sequence set forth in SEQ ID NO: 15, and the VL comprises an amino acid sequence set forth in SEQ ID NO: 16.

In some specific embodiments, provided is the anti-MASP2 antibody or the antigen-binding fragment thereof, wherein, a) the VH and the VL comprise or consist of amino acid sequences set forth in SEQ ID NOs: 7 and 8, respectively;

b) the VH and the VL comprise or consist of amino acid sequences set forth in SEQ ID NOs: 9 and 10, respectively;

c) the VH and the VL comprise or consist of amino acid sequences set forth in SEQ ID NOs: 11 and 12, respectively;

d) the VH and the VL comprise or consist of amino acid sequences set forth in SEQ ID NOs: 47 and 51, respectively;

e) the VH and the VL comprise or consist of amino acid sequences set forth in SEQ ID NOs: 47 and 52, respectively;

f) the VH and the VL comprise or consist of amino acid sequences set forth in SEQ ID NOs: 48 and 51, respectively;

g) the VH and the VL comprise or consist of amino acid sequences set forth in SEQ ID NOs: 48 and 52, respectively;

h) the VH and the VL comprise or consist of amino acid sequences set forth in SEQ ID NOs: 49 and 51, respectively;

i) the VH and the VL comprise or consist of amino acid sequences set forth in SEQ ID NOs: 49 and 52, respectively;

j) the VH and the VL comprise or consist of amino acid sequences set forth in SEQ ID NOs: 50 and 51, respectively;

k) the VH and the VL comprise or consist of amino acid sequences set forth in SEQ ID NOS: 50 and 52, respectively;

1) the VH and the VL comprise or consist of amino acid sequences set forth in SEQ ID NOs: 13 and 14, respectively;

m) the VH and the VL comprise or consist of amino acid sequences set forth in SEQ ID NOs: 42 and 45, respectively;

n) the VH and the VL comprise or consist of amino acid sequences set forth in SEQ ID NOs: 42 and 46, respectively;

o) the VH and the VL comprise or consist of amino acid sequences set forth in SEQ ID NOs: 43 and 45, respectively;

p) the VH and the VL comprise or consist of amino acid sequences set forth in SEQ ID NOs: 43 and 46, respectively;

q) the VH and the VL comprise or consist of amino acid sequences set forth in SEQ ID NOs: 44 and 45, respectively;

r) the VH and the VL comprise or consist of amino acid sequences set forth in SEQ ID NOs: 44 and 46, respectively; or s) the VH and the VL comprise or consist of amino acid sequences set forth in SEQ ID NOs: 15 and 16, respectively.

Further, the present disclosure provides an anti-MASP2 antibody or an antigen-binding fragment thereof comprising variants VH and VL having at least 80%, at least 85%, at least 90%, at least 91%, at least 92%, at least 93%, at least 94%, at least 95%, at least 96%, at least 97%, at least 98%, or at least 99% sequence identity to the VH and VL of any one of a) to s) described above, respectively.

In some embodiments, the anti-MASP2 antibody or the antigen-binding fragment thereof of the present disclosure is an IgG antibody or an antigen-binding fragment thereof, e.g., an IgG1, IgG2 or IgG4 antibody or an antigen-binding fragment thereof, e.g., an IgG4 antibody or an antigen-binding fragment thereof having any one or more mutations of S228P, F234A, and L235A in an Fc fragment. All the mutations described above are numbered according to the EU scheme.

In some embodiments, the anti-MASP2 antibody or the antigen-binding fragment thereof of the present disclosure further comprises a human immunoglobulin Fc region; for example, the Fc region is an Fc region of human IgG1, IgG2, or IgG4. In some embodiments, the Fc region may have a mutation that reduces ADCC function. In some embodiments, examples of the mutations include L234A/L235A on IgG1, V234A/G237A/P238S/H268A/V309L/A330S/P331S on IgG2, F234A/L235A on IgG4, S228P/F234A/L235A on IgG4, N297A on IgG1 IgG2, IgG3 or IgG4, V234A/G237A on IgG2, K214T/E233P/L234V/L235A/G236 deletion/A327G/P331A/D365E/L358M IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236 deletion/G237A/P238S on IgG4. Hybrid IgG2/4Fc domains may also be used, e.g., Fc with residues 117-260 from IgG2 and residues 261-447 from IgG4. In some specific embodiments, the Fc region of the human IgG4 has any one or more mutations of S228P, F234A, L235A, and K447A (see WO2017079112A, WO2018031400A, etc.).

In some embodiments, the antigen-binding fragment of the anti-MASP2 antibody of the present disclosure is Fab, Fv, sFv, Fab', F(ab')$_2$, a linear antibody, a single-chain antibody, scFv, sdAb, sdFv, a nanobody, a peptibody, a domain antibody, and a multispecific antibody (bispecific antibody, diabody, triabody, and tetrabody, tandem di-scFv, tandem tri-scFv), for example, specifically, an scFv, Fv, Fab or Fab' fragment.

In some embodiments, the antigen-binding fragment of the anti-MASP2 antibody of the present disclosure comprises: a full-length heavy chain comprising an amino acid sequence set forth in SEQ ID NO: 54 or an amino acid sequence having at least 80%, at least 90%, or at least 95% identity thereto, and a full-length light chain comprising an amino acid sequence set forth in SEQ ID NO: 55 or an amino acid sequence having at least 80%, at least 90%, or at least 95% identity thereto;

a full-length heavy chain comprising an amino acid sequence set forth in SEQ ID NO: 56 or an amino acid sequence having at least 80%, at least 90%, or at least 95% identity thereto, and a full-length light chain comprising an amino acid sequence set forth in SEQ ID NO: 57 or an amino acid sequence having at least 80%, at least 90%, or at least 95% identity thereto; or a full-length heavy chain comprising an amino acid sequence set forth in SEQ ID NO: 58 or an amino acid sequence having at least 80%, at least 90%, or at least 95% identity thereto, and a full-length light chain comprising an amino acid sequence set forth in SEQ ID NO: 59 or an amino acid sequence having at least 80%, at least 90%, or at least 95% identity thereto.

In some specific embodiments, the full-length heavy chain and light chain comprise amino acid sequences set forth in SEQ ID NOs: 54 and 55, respectively: the full-length heavy chain and light chain comprise amino acid sequences set forth in SEQ ID NOs: 56 and 57, respectively; or the full-length heavy chain and light chain comprise amino acid sequences set forth in SEQ ID NOs: 58 and 59, respectively.

In some embodiments, the anti-MASP2 antibody or the antigen-binding fragment thereof according to the present disclosure comprises a heavy chain variable region having 0 to 10 (1, 2, 3, 4, 5, 6, 7, 8, 9, 10) amino acid changes and a light chain variable region having 0 to 10 (1, 2, 3, 4, 5, 6, 7, 8, 9, 10) amino acid changes. In some specific embodiments, the amino acid changes are conservative replacements, substitutions or modifications, and/or deletions or additions that do not affect function.

In some embodiments, provided is an anti-MASP2 antibody or an antigen-binding fragment, which binds to or competes for binding to the same epitope as the anti-MASP2 antibody or the antigen-binding fragment described above.

In some embodiments, provided is an anti-MASP2 antibody or an antigen-binding fragment, which blocks the binding of the anti-MASP2 antibody or the antigen-binding fragment thereof described above to human MASP2.

In some embodiments, provided is an anti-MASP2 antibody or an antigen-binding fragment, the binding of which to human MASP2 is blocked by the anti-MASP2 antibody or the antigen-binding fragment thereof described above.

In some embodiments, the anti-MASP2 antibody or the antigen-binding fragment of the present disclosure has at least one of the following;

(i) the antibody or the antigen-binding fragment binding to human MASP-2 with $K_D$ of 10 nM or less;

(ii) the antibody or the antigen-binding fragment binding to an epitope in a CCP1 domain of MASP-2;

(iii) the antibody or the antigen-binding fragment inhibiting C3b deposition in 1% human serum in an in vitro assay with $IC_{50}$ of 10 nM or less, the $IC_{50}$ being capable of being determined, for example, by the method in Example 3 of the present disclosure;

(iv) the antibody or the antigen-binding fragment inhibiting C3b deposition in 90% human serum with $IC_{50}$ of 30 nM or less, the $IC_{50}$ being capable of being determined, for example, by the method in Example 6 of the present disclosure; and (v) the antibody or the antigen-binding fragment substantially having no inhibition of the classic pathway.

In some embodiments, the anti-MASP-2 antibody selectively inhibits MASP-2 complement activation, preserving the functional integrity of the C1q-dependent complement activation system.

In some embodiments, provided is an MASP2-binding protein or a binding molecule, which comprises any of the anti-MASP2 antibodies or the antigen-binding fragments thereof of the present disclosure described above.

In some specific embodiments, the MASP2-binding protein or the binding molecule contains one or more effector molecules selected from the group consisting of anti-tumor agents, drugs, toxins, biologically active proteins (e.g., enzymes), other antibodies or antibody fragments, synthetic or naturally occurring polymers, nucleic acids and fragments thereof such as DNA and RNA and fragments thereof, radionuclides (e.g., radioiodides), radioisotopes, chelated metals, nanoparticles and reporter groups (e.g., fluorescent compounds), or compounds that can be detected by NMR or ESR spectroscopy. In some specific embodiments, the effector molecule is conjugated or fused to the anti-MASP2 antibody or the antigen-binding fragment thereof of the present disclosure.

Polynucleotide and Vector

The present disclosure provides an isolated polynucleotide encoding the anti-MASP2 antibody or the antigen-binding fragment thereof, the binding protein, or the binding molecule of the present disclosure. The polynucleotide may be DNA or RNA. According to some embodiments of the present disclosure, the polynucleotide of the present disclosure is a substantially isolated or isolated polynucleotide.

The present disclosure provides an expression vector containing the polynucleotide described above, or alternatively, the polynucleotide of the present disclosure may be in the form of, may be present in, and/or may be part of a vector, such as a plasmid, cosmid, YAC, or viral vector. The vector may be particularly an expression vector, i.e., a vector that can provide expression of the anti-MASP2 antibody or the antigen-binding fragment thereof in vitro and/or in vivo (i.e., in a suitable host cell, host organism, and/or expression system). The expression vector may be a eukaryotic expression vector, a prokaryotic expression vector, or a viral vector, e.g., a plasmid, cosmid, or phage. The expression vector generally comprises at least one of the polynucleotides of the present disclosure, which is operably linked to one or more suitable expression regulatory elements (e.g., promoters, enhancers, terminators, and the like). The selection of the elements and their sequences for expression in a particular host is within the knowledge of those skilled in the art. Regulatory elements and other elements useful or necessary for expression of the PD-1-binding protein of the present disclosure include, for example, promoters, enhancers, terminators, integration factors, selection labels, leader sequences, and reporter genes.

The polynucleotide of the present disclosure may be prepared or obtained by known means (e.g., by automatic DNA synthesis and/or recombinant DNA techniques) based on information on the amino acid sequence of the polypeptide of the present disclosure, and/or may be isolated from a suitable natural source.

Host Cell

The present disclosure provides a host cell expressing the anti-MASP2 antibody or the antigen-binding fragment thereof, the binding protein, or the binding molecule of the present disclosure, and/or containing the polynucleotide or the vector of the present disclosure. In some embodiments, the host cell is a bacterial cell, a fungal cell, or a mammalian cell Bacterial cells include, for example, cells of gram-negative bacterial strains (e.g., *Escherichia coli* strains, *Proteus* strains, and *Pseudomonas* strains), and gram-positive bacterial strains (e.g., *Bacillus* strains, *Streptomyces* strains, *Staphylococcus* strains, and *Lactococcus* strains).

Fungal cells include, for example, cells of species of *Trichoderma, Neurospora*, and *Aspergillus*; or cells of species of *Saccharomyces* (e.g., *Saccharomyces cerevisiae*), *Schizosaccharomyces* (e.g., *Schizosaccharomyces pombe*), *Pichia* (*Pichia pastoris* and *Pichia methanolica*), and *Hansenula.*

Mammalian cells include, for example, HEK293 cells, CHO cells, BHK cells, HeLa cells, COS cells, and the like.

However, amphibian cells, insect cells, plant cells, and any other cells used in the art for expressing heterologous proteins may also be used in the present disclosure.

The cells of the present disclosure are unable to develop into a finished plant or individual animal.

Production or Preparation Method

The present disclosure provides a method for preparing the anti-MASP2 antibody or the antigen-binding fragment thereof, the binding protein, or the binding molecule of the present disclosure, which generally comprises the following steps:

- culturing the host cell of the present disclosure under conditions that allow expression of the anti-MASP2 antibody or the antigen-binding fragment thereof, the binding protein, or the binding molecule of the present disclosure;
- isolating a target protein expressed by the host cell from the culture; and
- optionally, further purifying and/or modifying the target protein of the present disclosure.

The anti-MASP2 antibody or the antigen-binding fragment thereof, the binding protein, or the binding molecule of the present disclosure can be produced intracellularly (e.g., in the cytoplasm, in the periplasm, or in inclusion bodies) in the cell described above, followed by isolation from the host cell and optionally further purification; or it may be produced extracellularly (e.g., in the medium in which the host cell is cultured), followed by isolation from the medium and optionally further purification.

Methods and reagents for recombinant production of polypeptides, e.g., specific suitable expression vectors, transformation or transfection methods, selection labels, methods for inducing protein expression, culture conditions, and the like, are known in the art. Similarly, protein isolation and purification techniques suitable for use in the method for producing the protein of the present disclosure are well known to those of skill in the art. As an example, cDNA sequences encoding the heavy and light chains can be cloned and recombined into an expression vector. Recombinant immunoglobulin expression vectors can be stably transfected into CHO cells. Mammalian expression systems may result in glycosylation of antibodies, particularly at the highly conserved N-terminus of the Fc region. Stable clones are obtained by expression of antibodies specifically binding to the human-derived antigen. Positive clones are expanded in a serum-free medium of a bioreactor to produce antibodies. The culture medium with the secreted antibody can be purified and collected by conventional techniques. The antibody can be filtered and concentrated by conventional methods. Soluble mixtures and polymers can also be removed by conventional methods, such as molecular sieves and ion exchange. The resulting product needs to be immediately frozen, e.g., at −70° C., or lyophilized.

However, the anti-MASP2 antibody or the antigen-binding fragment thereof, the binding protein, or the binding molecule of the present disclosure may also be obtained by other methods for producing proteins known in the art, such as chemical synthesis, including solid-phase or liquid-phase synthesis.

Composition

The present disclosure provides a composition, e.g., a pharmaceutical composition, which comprises a therapeutically effective amount of the anti-MASP2 antibody or the antigen-binding fragment thereof, the binding protein, or the binding molecule described above, and one or more pharmaceutically acceptable carriers, diluents, buffers, or excipients.

In some specific embodiments, the pharmaceutical composition may contain 0.01 wt % to 99 wt % of the anti-MASP2 antibody or the antigen-binding fragment thereof in a unit dose, or the pharmaceutical composition may contain 0.1-2000 mg, and in some specific embodiments, 1-1000 mg, of the anti-MASP2 antibody or the antigen-binding fragment thereof in a unit dose.

Kit (or Kit-of-Parts)

The present disclosure provides a kit or kit-of-parts, which comprises one or more containers each independently comprising any one or a combination thereof selected from the group consisting of: the anti-MASP2 antibody or the antigen-binding fragment thereof, the binding protein, the binding molecule, and the polynucleotide encoding the above protein or molecule or antibody or the antigen-binding fragment of the present disclosure.

In some embodiments, further provided are a diagnostic reagent comprising the polynucleotide described above and related diagnostic use.

Method for Preventing and Treating Disease and Pharmaceutical Use

The present disclosure provides use and method of the anti-MASP2 antibody or the antigen-binding fragment thereof, the binding protein, the binding molecule, the polynucleotide, and the pharmaceutical composition of the present disclosure in the prevention and/or treatment of a disease, which may or may not be related to the complement signaling pathway (e.g., MASP2). In some embodiments, the disease is IgA nephropathy or paroxysmal nocturnal hemoglobinuria (PNH).

The present disclosure provides a method for treating or preventing a disease, which comprises administering to a subject in need thereof a therapeutically or prophylactically effective amount of the anti-MASP2 antibody or the antigen-binding fragment thereof, the binding protein, the binding molecule, the polynucleotide, and/or the pharmaceutical composition of the present disclosure.

The present disclosure provides a method for inhibiting MASP-2-dependent complement activation in a subject, which comprises administering to the subject the anti-MASP2 antibody or the antigen-binding fragment thereof, the binding protein, the binding molecule, the polynucleotide, and/or the pharmaceutical composition of the present disclosure in an effective amount (e.g., an amount sufficient to inhibit the MASP-2-dependent complement activation).

MASP-2-dependent complement activation has been indicated to contribute to the pathogenesis of many acute and chronic disease states, including MASP-2-dependent complement-mediated vascular conditions, ischemia reperfusion injury, atherosclerosis, inflammatory gastrointestinal disorders, pulmonary conditions, extracorporeal reperfusion processes, skeletal muscle conditions, renal conditions, skin conditions, organ or tissue transplantation, nervous system disorders or injuries, blood disorders, genitourinary tract conditions, diabetes, chemotherapy or radiation therapy, malignant tumors, endocrine disorders, coagulation disorders, or ophthalmic conditions. In some embodiments, provided are a method of the anti-MASP2 antibody or the antigen-binding fragment thereof, the binding protein, the binding molecule, the polynucleotide, and/or the pharmaceutical composition of the present disclosure for treating the diseases and conditions described above, and related pharmaceutical use.

In some embodiments, the diseases and conditions described above are diseases related to MASP-2-dependent complement activation.

In some embodiments, the diseases and conditions described above are microvascular endothelial cell damage and/or thrombosis.

In some embodiments, the diseases and conditions described above are selected from the group consisting of: IgA nephropathy, paroxysmal nocturnal hemoglobinuria (PNH), lupus nephritis, thrombotic microangiopathy (TMA) (e.g., hematopoietic stem cell transplantation-associated thrombotic microangiopathy (HSCT-TMA) or thrombotic thrombocytopenia purpura (TTP)), hemolytic uremic syndrome (HUS), membranous glomerulonephritis, glomerulonephritis, age-related macular degeneration, reperfusion injury, myocardial infarction, diabetic neuropathy, stroke, graft-versus-host disease (GVHD), and Upshaw-Schulman syndrome (USS): in some specific embodiments, the diseases are related to the MASP-2-dependent complement activation.

Detection

The present disclosure provides a composition for detecting MASP2, which comprises the anti-MASP2 antibody or the antigen-binding fragment thereof according to the present disclosure. The present disclosure further provides a method, system or device for detecting MASP2 in vivo or in vitro, which comprises treating a sample with the anti-MASP2 antibody or the antigen-binding fragment thereof of the present disclosure.

In some embodiments, the method, system or device for detecting MASP2 in vitro may, for example, comprise;

(1) contacting a sample with an MASP2-binding antibody or an antigen-binding fragment thereof;
(2) detecting formation of a complex between the MASP2-binding antibody or the antigen-binding fragment thereof and the sample; and/or
(3) contacting a reference sample (e.g., a control sample) with the antibody; and
(4) determining the extent of formation of the complex by comparison with the reference sample. A change (e.g., a statistically significant change) in the formation of the complex in the sample or subject as compared to a control sample or subject indicates the presence of MASP2 in the sample.

In some other embodiments, the method, system or device for detecting MASP2 in vivo may comprise;

(1) administering to a subject an MASP2-binding antibody or an antigen-binding fragment thereof; and
(2) detecting formation of a complex between the MASP2-binding antibody or the antigen-binding fragment thereof and the subject.

The detection may include determining the location or time at which the complex is formed. The MASP2 antibody is labeled with a detectable substance, and the label is detected to achieve detection of the substance that binds to the MASP2 antibody (e.g., MASP2). Suitable detectable substances include various enzymes, prosthetic groups, fluorescent substances, luminescent substances, and radioactive substances. The formation of the complex between the MASP2-binding antibody or the antigen-binding fragment thereof and MASP2 may be detected by determining or visualizing the antibody that binds to or does not bind to MASP2. Conventional detection assays may be used, such as enzyme-linked immunosorbent assay (ELISA), radioimmunoassay (RIA) or tissue immunohistochemistry. For detection purposes, the anti-MASP2 antibody or the fragment thereof of the present disclosure may be labeled with a fluorophore chromophore.

In some embodiments, further provided is a kit, which comprises an anti-MASP2 antibody or an antigen-binding fragment thereof, and may also comprise instructions for diagnostic use. The kit may also comprise at least one additional reagent, such as a label or an additional diagnostic agent. For in vivo use, the antibody may be formulated into a pharmaceutical composition.

Definition of Terms

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

The three-letter and single-letter codes for amino acids used herein are as described in *J. biol. chem,* 243, p3558 (1968).

"MASP-2-dependent complement activation" includes MASP-2-dependent activation of the lectin pathway, which occurs under physiological conditions (i.e., in the presence of Ca++), resulting in the formation of a C3 convertase C4b2a of the lectin pathway, and after accumulation of the C3 cleavage product C3b, resulting in a C5 convertase C42a(C3b)n.

"Classic pathway" refers to complement activation triggered by binding of an antibody to exogenous particles and requiring binding to a recognition molecule C1q. "Alternative pathway" refers to complement activation, which is triggered, for example, by zymosan from fungal and yeast cell walls, lipopolysaccharide (LPS) from the outer membrane of gram-negative bacteria, and rabbit erythrocytes, as well as many pure polysaccharides, rabbit erythrocytes, viruses, bacteria, animal tumor cells, parasites, and damaged cells, and has traditionally been regarded as resulting from spontaneous proteolysis of the complement factor C3 to produce C3b. "Lectin pathway" refers to complement activation, which occurs via specific binding of serum to non-serum carbohydrate-binding proteins, including mannan-binding lectin (MBL), CL-11, and ficolin (H-ficolin, M-ficolin, or L-ficolin).

"Antibody" is used in the broadest sense and encompasses a variety of antibody structures, including, but not limited to monoclonal antibodies, polyclonal antibodies; monospecific antibodies, multispecific antibodies (e.g., bispecific antibodies); and full-length antibodies, and antibody fragments (or antigen-binding fragments, or antigen-binding portions) so long as they exhibit the desired antigen-binding activity. An antibody may refer to an immunoglobulin, which is of a tetrapeptide chain structure formed by connection between two identical heavy chains and two identical light chains by interchain disulfide bonds. The heavy chain constant regions of an immunoglobulin differ in their amino acid composition and arrangement, and thus in their antigenicity. Accordingly, immunoglobulins can be divided into five classes, or isotypes of immunoglobulins, namely IgM, IgD, IgG, IgA and IgE, with their corresponding heavy chains being μ chain, δ chain, γ chain, α chain and ε chain, respectively. Ig of the same class can be divided into different subclasses according to differences in the amino acid composition of the hinge regions and the number and positions of disulfide bonds of the heavy chains; for example, IgG can be divided into IgG1, IgG2, IgG3 and IgG4. Light chains are divided into κ or λ chains according to differences in the constant regions. Each of the five classes of Ig may have a κ chain or λ chain. In the antibody heavy and light chains, the sequences of about 110 amino acids near the N-terminus vary considerably and thus are referred to as variable regions (V regions): the remaining amino acid sequences near the C-terminus are relatively stable and thus are referred to as constant regions (C regions). The variable regions comprise 3 hypervariable regions (CDRs) and 4 framework regions (FRs) with relatively conservative sequences. The 3 hypervariable regions determine the specificity of the antibody and thus are also known as complementarity determining regions (CDRs). Each of the light chain variable regions (VLs) and the heavy chain variable regions (VHs) consists of 3 CDR regions and 4 FR regions arranged from the amino terminus to the carboxyl terminus in the following order: FR1, CDR1, FR2, CDR2, FR3, CDR3, and FR4. The 3 CDR regions of the light chain refer to LCDR1, LCDR2, and LCDR3; and the 3 CDR regions of the heavy chain refer to HCDR1, HCDR2, and HCDR3.

For determination or definition of "CDRs", the deterministic depiction of CDRs and identification of residues comprising antigen-binding sites of the antibody can be accomplished by resolving the structure of the antibody and/or resolving the structure of the antibody-ligand complex. This can be accomplished by any of a variety of techniques known to those skilled in the art, such as X-ray crystallography. A variety of analysis methods can be used to identify CDRs, including but not limited to Kabat numbering scheme, Chothia numbering scheme, AbM numbering scheme, IMGT numbering scheme, contact definition, and conformational definition.

The Kabat numbering scheme is a standard for numbering residues in antibodies and is generally used to identify CDR regions (see, e.g., Johnson & Wu, 2000, *Nucleic Acids Res.*, 28: 214-8). The Chothia numbering scheme is similar to the Kabat numbering scheme, except that it takes into account the position of certain structural loop regions. (see, e.g., Chothia et al., 1986, *J. Mol. Biol.*, 196: 901-17: Chothia et al., 1989, *Nature*, 342: 877-83). The AbM numbering scheme adopts a computer program integration suite for modeling antibody structures manufactured by Oxford Molecular Group (see, e.g., Martin et al., 1989, *Proc Natl Acad Sci* (USA), 86: 9268-9272: "AbM™, A Computer Program for Modeling Variable Regions of Antibodies", Oxford, UK: Oxford Molecular, Ltd.). The AbM numbering scheme adopts a combination of a knowledge database and the de-novo method to model the tertiary structure of antibodies from basic sequences (see those described in Samudrala et al., 1999, "Ab Initio Protein Structure Prediction Using a Combined Hierarchical Approach", *PROTEINS. Structure. Function and Genetics Suppl.*, 3: 194-198). The contact definition is based on the analysis of the available complex crystal structures (see, e.g., MacCallum et al., 1996, *J. Mol. Biol.*, 5: 732-45). In the conformational definition, the positions of the CDRs can be identified as residues that contribute enthalpy to the antigen binding (see, e.g., Makabe et al., 2008, *Journal of Biological Chemistry*, 283: 1156-1166). In addition, other CDR boundary definitions may not strictly follow one of the above methods, but still overlap with at least a portion of the Kabat CDRs, although they may be shortened or lengthened based on predictions or experimental results that a particular residue or a particular group of residues does not significantly affect the antigen binding. As used herein, a CDR may refer to a CDR defined by any method known in the art, including combinations of methods.

The CDR amino acid residues of the VL and VH regions of the antibody or the antigen-binding fragment of the present disclosure correspond with known Kabat or AbM numbering scheme in terms of number and positions.

"Monoclonal antibody" or "mAb" refers to an antibody obtained from a population of substantially homogeneous antibodies, that is, the antibodies comprised in the population are identical except for naturally occurring mutations that may be present in minor amounts. Monoclonal antibodies are highly specific and directed against a single antigen site. Furthermore, in contrast to polyclonal antibody preparations which generally include different antibodies directed against different determinants (epitopes), each monoclonal antibody is directed against a single determinant on the antigen. The modifier "monoclonal" indicates the characteristics of an antibody obtained from a population of substantially homogeneous antibodies, and is not to be construed as requiring production of the antibody by any particular method. For example, monoclonal antibodies used according to the present disclosure can be prepared by the hybridoma methods first described in Kohler and Milstein, 1975, *Nature* 256: 495, or can be prepared by the recombinant DNA method described in U.S. Pat. No. 4,816,567. For example, monoclonal antibodies can also be isolated from the generated phage library using the technique described in McCafferty et al., 1990, *Nature* 348: 552-554.

"Fully human antibody" or "recombinant fully human antibody" includes fully human antibodies prepared, expressed, created, or isolated by recombinant methods, involving techniques and methods well known in the art, such as;

(1) antibodies isolated from transgenic human immunoglobulin genes, transchromosomal animals (e.g., mice), or hybridomas prepared therefrom;
(2) antibodies isolated from host cells that have been transformed to express the antibodies, such as transfectomas;
(3) antibodies isolated from a recombinant combinatorial fully human antibody library; and
(4) antibodies prepared, expressed, created, or isolated by a method such as splicing human immunoglobulin gene sequences to other DNA sequences.

Such recombinant fully human antibodies comprise variable and constant regions that utilize particular human germline immunoglobulin sequences encoded by germline genes, and also include subsequent rearrangements and mutations which occur, for example, during antibody maturation.

The term "murine antibody" herein refers to a monoclonal antibody directed against human MASP2 or an epitope thereof prepared according to the knowledge and skill in the art. During the preparation, a test subject is injected with an MASP2 antigen, and then hybridomas expressing antibodies with desired sequences or functional properties are isolated. In a specific embodiment of the present disclosure, the murine anti-human MASP2 antibody or the antigen-binding fragment thereof may further comprise a light chain constant region of a murine κ or λ chain or a variant thereof, or further comprise a heavy chain constant region of a murine IgG1, IgG2, IgG3 or IgG4 or a variant thereof.

The term "fully human antibody" includes antibodies having variable and constant regions derived from human germline immunoglobulin sequences. The fully human antibody of the present disclosure may include amino acid residues not encoded by human germline immunoglobulin sequences (e.g., mutations introduced by random or site-specific mutagenesis in vitro or by somatic mutations in vivo). However, the term "fully human antibody" does not include antibodies in which CDR sequences derived from the germline of another mammalian species (such as mice) have been grafted into human framework sequences (i.e., "humanized antibody").

The term "humanized antibody", also known as a CDR-grafted antibody, refers to an antibody produced by grafting non-human CDR sequences into the framework of variable regions of a human antibody. Such an antibody can overcome the strong immune response induced by the chimeric antibody because of carrying a large number of non-human protein components. To avoid the decrease in activity caused by the decrease in immunogenicity, the variable regions of a fully human antibody can be subjected to minimum reverse mutation to maintain activity.

The term "chimeric antibody" refers to an antibody obtained by fusing variable regions of an antibody of a first species to constant regions of an antibody of a second species, which can reduce an immune response induced by the antibody of the first species. As an example, the chimeric antibody is established by firstly establishing a hybridoma secreting a murine-specific monoclonal antibody, then cloning a variable region gene from the mouse hybridoma cells, cloning a constant region gene of a fully human antibody as required, linking the mouse variable region gene and the human constant region gene to form a chimeric gene, inserting the chimeric gene into a human vector, and finally expressing chimeric antibody molecules in a eukaryotic industrial system or prokaryotic industrial system. The constant region of the fully human antibody may be selected from the group consisting of the heavy chain constant regions of human IgG1, IgG2, IgG3 and IgG4 or variants thereof, preferably comprising human IgG2 or IgG4 heavy chain constant regions, or IgG1 mutated at amino acids without ADCC (antibody-dependent cell-mediated cytotoxicity) toxicity.

"Antigen-binding fragment" includes a single-chain antibody (i.e., full-length heavy and light chains); Fab, a modified Fab, Fab', a modified Fab', $F(ab')_2$, Fv, Fab-Fv, Fab-dsFv, a single-domain antibody (e.g., VH or VL or VHH), scFv, a bivalent or trivalent or tetravalent antibody, Bis-scFv, a diabody, a tribody, a triabody, a tetrabody and an epitope-binding fragment of any one of the above (see, e.g., Holliger and Hudson, 2005, *Nature Biotech.* 23 (9): 1126-1136; Adair and Lawson, 2005, *Drug Design Reviews-Online* 2 (3), 209-217). Methods for producing and preparing such antibody fragments are well known in the art (see, e.g., Verma et al., 1998, *Journal of Immunological Methods,* 216, 165-181). Fab-Fv was first disclosed in WO2009/040562, and its disulfide-stabilized form Fab-dsFv was first disclosed in WO2010/035012. The antigen-binding fragment of the present disclosure also includes Fab and Fab' fragments described in WO2005/003169, WO2005/003170 and WO2005/003171. Multivalent antibodies may comprise multiple specificities (e.g., bispecificites) or may be monospecific (see, e.g., WO92/22583 and WO05/113605), and an example of the latter is Tri-Fab (or TFM) described in WO92/22583.

The term "binding to MASP2" herein refers to the ability to interact with MASP2 or an epitope thereof, wherein the MASP2 or the epitope thereof may be derived from humans. The term "antigen-binding site" herein refers to a discontinuous three-dimensional spatial site on an antigen that is recognized by the antibody or the antigen-binding fragment of the present disclosure.

"Antigen" refers to a molecule used for immunization of an immunocompetent vertebrate to produce an antibody that recognizes the antigen or to screen an expression library (e.g., particularly phage, yeast or ribosome display library). Herein, the antigen is defined in a broader sense, and includes a target molecule that is specifically recognized by the antibody, and a portion or a mimic of a molecule used in an immunization process for producing the antibody or in library screening for selecting the antibody. For the antibody of the present disclosure that binds to human MASP2, monomers and polymers (e.g., dimers, trimers, etc.) of human MASP2, and truncated variants and other variants of human MASP2 are all referred to as antigens.

The term "epitope" refers to a site on an antigen to which an immunoglobulin or an antibody binds. An epitope may be formed from contiguous amino acids, or non-contiguous amino acids juxtaposed by tertiary folding of the protein. An epitope formed from contiguous amino acids is generally retained after exposure to a denaturing solvent, while an epitope formed by tertiary folding is generally lost after a denaturing solvent treatment. An epitope generally comprises at least 3-15 amino acids in a unique spatial conformation. Methods for determining what epitope is bound by a given antibody are well known in the art and include an immunoblotting assay, an immunoprecipitation assay, and the like. Methods for determining the spatial conformation of an epitope include techniques in the art and techniques described herein, such as X-ray crystallography and two-dimensional nuclear magnetic resonance.

"Specific binding" or "selective binding" refers to binding of an antibody to an epitope on a predetermined antigen. Generally, an antibody binds to a predetermined antigen or epitope thereof with an equilibrium dissociation constant ($K_D$) of about less than $10^{-7}$ M or even less and with an affinity that is at least twice as high as its affinity for binding to a non-specific antigen other than the predetermined antigen or the epitope thereof (or non-specific antigens other than closely related antigens, e.g., BSA, etc.), when determined by surface plasmon resonance (SPR) techniques in an instrument using human MASP2 or an epitope thereof as an analyte and the antibody as a ligand. The term "antigen-recognizing antibody" is used interchangeably herein with the term "specifically bound antibody".

"Binding affinity" or "affinity" is used herein as a measure of the strength of a non-covalent interaction between two molecules (e.g., an antibody or a portion thereof and an antigen). The binding affinity between two molecules can be quantified by determining the dissociation constant ($K_D$). $K_D$ can be determined by measuring the kinetics of complex formation and dissociation using, for example, the surface plasmon resonance (SPR) method (Biacore). The rate constants corresponding to the association and dissociation of a monovalent complex are referred to as the association rate constant ka (or kon) and the dissociation rate constant kd (or koff), respectively. $K_D$ is related to ka and kd by the equation $K_D$=kd/ka. The value of the dissociation constant can be determined directly by well-known methods and can be calculated by methods such as those described by Caceci et al. (1984, *Byte* 9: 340-362) even for complex mixtures. For example, $K_D$ can be determined by using a dual filtration nitrocellulose filter binding assay such as that disclosed by Wong & Lohman (1993, *Proc. Natl. Acad. Sci. USA* 90: 5428-5432). Other standard assays for evaluating the binding ability of an antibody to a target antigen are known in the art and include, for example, ELISA, western blot, RIA and flow cytometry, as well as other assays exemplified elsewhere herein. The binding kinetics and binding affinity of the antibody can also be evaluated by standard assay's known in the art, such as surface plasmon resonance (SPR), for example, by using the Biacore™ system or KinExA. The binding affinities associated with different molecular interactions, e.g., the binding affinities of different antibodies for a given antigen, can be compared by comparing the $K_D$ values of antibody/antigen complexes. Similarly, the specificity of an interaction can be evaluated by determining and comparing the $K_D$ value for the interaction of interest (e.g., a specific interaction between an antibody and an antigen) with the $K_D$ value for an interaction not of interest (e.g., a control antibody known not to bind to MASP2).

"Conservative replacement" refers to replacement by another amino acid residue having similar properties to the original amino acid residue. For example, lysine, arginine and histidine have similar properties in that they have basic side chains, and aspartic acid and glutamic acid have similar properties in that they have acidic side chains. In addition, glycine, asparagine, glutamine, serine, threonine, tyrosine, cysteine and tryptophan have similar properties in that they have uncharged polar side chains, and alanine, valine, leucine, threonine, isoleucine, proline, phenylalanine and methionine have similar properties in that they have non-polar side chains. In addition, tyrosine, phenylalanine, tryptophan and histidine have similar properties in that they have aromatic side chains. Thus, it will be apparent to those skilled in the art that even when an amino acid residue in a group exhibiting similar properties as described above is replaced, it will not exhibit a particular change in properties.

The term "cross-reactivity" refers to the ability of the antibody of the present disclosure to bind to MASP2 from different species. For example, the antibody of the present disclosure that binds to human MASP2 may also bind to MASP2 from another species. Cross-reactivity is determined by detecting specific reactivity with a purified antigen in binding assay's (e.g., SPR and ELISA) or binding or functional interactions with cells physiologically expressing MASP2. Methods for determining cross-reactivity include standard binding assays as described herein, for example, surface plasmon resonance analysis or flow cytometry.

The terms "inhibition" and "blocking" are used interchangeably and encompass both partial and complete inhibition/blocking. Inhibition/blocking of MASP2 preferably reduces or alters the normal level or type of activity that occurs when MASP2 binding occurs without inhibition or blocking. Inhibition and blocking are also intended to include any measurable decrease in MASP2 binding affinity when in contact with an anti-MASP2 antibody as compared to MASP2 not in contact with an anti-MASP2 antibody.

"Inhibition of growth" (e.g., involving cells) is intended to include any measurable reduction in cell growth.

Methods for producing and purifying antibodies and antigen-binding fragments are well known in the prior art and can be found in, for example, "Antibodies: A Laboratory Manual", Cold Spring Harbor Press (chapters 5-8 and 15). For example, mice can be immunized with human MASP2 or a fragment thereof, and the resulting antibodies can be renatured and purified, and amino acid sequencing can be performed by conventional methods. Likewise, antigen-binding fragments can be prepared by conventional methods. The antibody or the antigen-binding fragment described herein is genetically engineered to contain one or more human FR regions in the non-human CDR regions. Human FR germline sequences are available from the ImMunoGeneTics (IMGT) website.

The engineered antibody or antigen-binding fragment of the present disclosure can be prepared and purified by conventional methods. For example, cDNA sequences encoding the heavy and light chains can be cloned and recombined into an expression vector. Recombinant immunoglobulin expression vectors can be stably transfected into cells. Mammalian expression systems may result in glycosylation of antibodies, particularly at the highly conserved N-terminus of the Fc region. Stable clones are obtained by expression of antibodies specifically binding to the human-derived antigen. Positive clones are expanded in a serum-free medium of a bioreactor to produce antibodies. The culture medium with the secreted antibody can be purified and collected by conventional techniques. The antibody can be filtered and concentrated by conventional methods. Soluble mixtures and polymers can also be removed by conventional methods, such as molecular sieves and ion exchange. The resulting product needs to be immediately frozen, e.g., at −70° C., or lyophilized.

Antibodies can be competitively screened for binding to the same epitope using conventional techniques known to those skilled in the art. For example, competition and cross-competition studies can be performed to obtain antibodies that compete or cross-compete with one another for binding to an antigen. A high-throughput method for obtaining antibodies that bind to the same epitope based on their cross-competition is described in International Patent Publication No. WO03/48731. Therefore, an antibody and an antigen-binding fragment thereof that competes for binding to the same epitope on MASP2 with the antibody molecule of the present disclosure can be obtained by conventional techniques known to those skilled in the art.

"Giving", "administering", and "treating", when applied to animals, humans, experimental subjects, cells, tissues, organs or biological fluid, refer to contact of an exogenous drug, a therapeutic agent, a diagnostic agent or a composition with the animals, humans, subjects, cells, tissues, organs or biological fluid. “Giving”, “administering”, and “treating” can refer to, for example, therapeutic, pharmacokinetic, diagnostic, research, and experimental methods. The treatment of cells comprises contacting the reagent with the cells and contacting the reagent with fluid, where the fluid is in contact with the cells. “Giving”, “administering”, and “treating” also refer to treating, e.g., a cell, by a reagent, diagnosis, a binding composition, or by another cell in vitro and ex vivo. “Treating”, when applied to humans, veterinary or research subjects, refers to therapeutic treatment, preventive or prophylactic measures, and research and diagnostic applications.

“Treatment” refers to administering a therapeutic agent, such as a composition comprising any of the antibodies or the antigen-binding fragments thereof of the present disclosure or conjugates thereof, either internally or externally to a subject who has had, is suspected of having, or is predisposed to having one or more diseases or symptoms thereof on which the therapeutic agent is known to have a therapeutic effect. Generally, the therapeutic agent is administered in an amount effective to alleviate one or more symptoms of the disease in the subject or population being treated, whether by inducing regression of such symptoms or inhibiting the development of such symptoms into any clinically measurable degree. The amount of therapeutic agent effective to alleviate any particular symptom of the disease (also referred to as the “therapeutically effective amount”) may vary depending on factors such as the disease state, age and weight of the subject, and the ability of the drug to produce a desired therapeutic effect in the subject. Whether a symptom of a disease has been alleviated can be evaluated by any clinical testing methods commonly used by doctors or other health care professionals to evaluate the severity or progression of the symptom. Although embodiments of the present disclosure (e.g., treatment methods or articles) may be ineffective in alleviating symptoms of a disease of interest in a certain subject, they shall alleviate the symptoms of the disease of interest in a statistically significant number of subjects as determined by any statistical test method known in the art, such as the Student’s t-test, Chi-square test, U-test by Mann and Whitney, Kruskal-Wallis test (H-test), Jonckheere-Terpstra test and Wilcoxon test.

“Effective amount” comprises an amount sufficient to ameliorate or prevent a symptom or sign of a medical condition. An effective amount also refers to an amount sufficient to allow or facilitate diagnosis. The effective amount for a particular subject or veterinary subject may vary depending on the factors such as the disorder to be treated, the general health of the subject, the method and route and dosage of administration, and the severity of side effects. An effective amount may be the maximum dose or administration regimen to avoid significant side effects or toxic effects.

“Homology” or “identity” refers to sequence similarity between two polynucleotide sequences or between two polypeptides. When positions in two compared sequences are occupied by identical nucleotides or amino acid monomer subunits, e.g., if the position of each of two DNA molecules is occupied by an identical nucleotide, the molecules are homologous at that position. The homology percentage between two sequences is a function of the number of matching or homologous positions shared by the two sequences divided by the number of positions compared×100%. For example, if 6 out of 10 positions are matched or homologous when two sequences are optimally aligned, the two sequences are 60% homologous. Generally, when two sequences are aligned, comparison is performed to obtain the maximum homology percentage.

“Cell”, “cell line”, and “cell culture” are used interchangeably, and all such designations include their progenies. It should also be understood that all progenies may not be precisely identical in DNA content due to intentional or unintentional mutations. Mutant progeny with identical function or biological activity as screened in the original transformed cells is included.

“Pharmaceutically acceptable carrier” or “pharmaceutically acceptable excipient” includes any material that, when combined with an active ingredient, allows the ingredient to retain biological activity and is non-reactive with the immune system of a subject. Examples include, but are not limited to, any standard pharmaceutical carrier, such as a phosphate buffered saline solution, water, an emulsion such as an oil/water emulsion, and various types of wetting agents. In some embodiments, the diluent for aerosol or parenteral administration is phosphate buffered saline (PBS) or normal (0.9%) saline. Compositions containing such carriers are formulated by well-known conventional methods (see, e.g., *Remington’s Pharmaceutical Sciences,* $18^{th}$ edition, A. Gennaro, eds., Mack Publishing Co., Easton, PA, 1990; and R Remington, *The Science and Practice of Pharmacy,* $20^{th}$ edition, Mack Publishing, 2000).

“Optional” or “optionally” means that the event or circumstance subsequently described may, but does not necessarily, occur, and that the description includes instances where the event or circumstance occurs or does not occur. For example, “optionally comprising 1-3 antibody heavy chain variable regions” means that the antibody heavy chain variable region of a particular sequence may, but not necessarily, be present.

“MASP2-binding protein” or “MASP2-binding molecule” of the present disclosure is interpreted in a maximized sense, and includes the anti-MASP2 antibody or the antigen-binding fragment thereof of the present disclosure, and any protein capable of achieving binding to MASP2 is within the scope of the term. For example, an MASP2-binding protein (or binding molecule) may comprise one or more effector molecules, e.g., in the form of a conjugate or fusion. The “effector molecules” include, for example, antitumor agents, drugs, toxins, biologically active proteins (e.g., enzymes), other antibody or antibody fragments, synthetic or naturally occurring polymers, nucleic acids and fragments thereof (DNA and RNA and fragments thereof), radionuclides (particularly radioiodides), radioisotopes, chelated metals, nanoparticles and reporter groups (e.g., fluorescent compounds) or compounds that can be detected by NMR or ESR spectroscopy. When the effector molecule is a polymer, it may generally be a synthetic or naturally occurring polymer, for example, an optionally substituted straight or branched chain polyalkylene, polyalkenylene or polyoxyalkylene polymer or a branched or unbranched polysaccharide, such as a homo-polysaccharide or a hetero-polysaccharide. Specific optional substituents that may be present on the synthetic polymers described above include one or more hydroxyl, methyl or methoxy groups. Specific examples of synthetic polymers include optionally substituted linear or branched poly(ethylene glycol), poly(propylene glycol) or poly(vinyl alcohol) or a derivative thereof, in particular optionally substituted poly(ethylene glycol), e.g., methoxy poly(ethylene glycol), or a derivative thereof. Specific naturally occurring polymers include lactose, amylose, dextran or glycogen or a derivative thereof. In one embodiment, the polymer is albumin or a fragment thereof, e.g., human serum albumin or a fragment thereof. Conjugation of the polymer to the anti-MASP2 antibody or the antigen-binding fragment thereof of the present disclosure can be achieved by conventional methods.

DETAILED DESCRIPTION

Figure 1A:
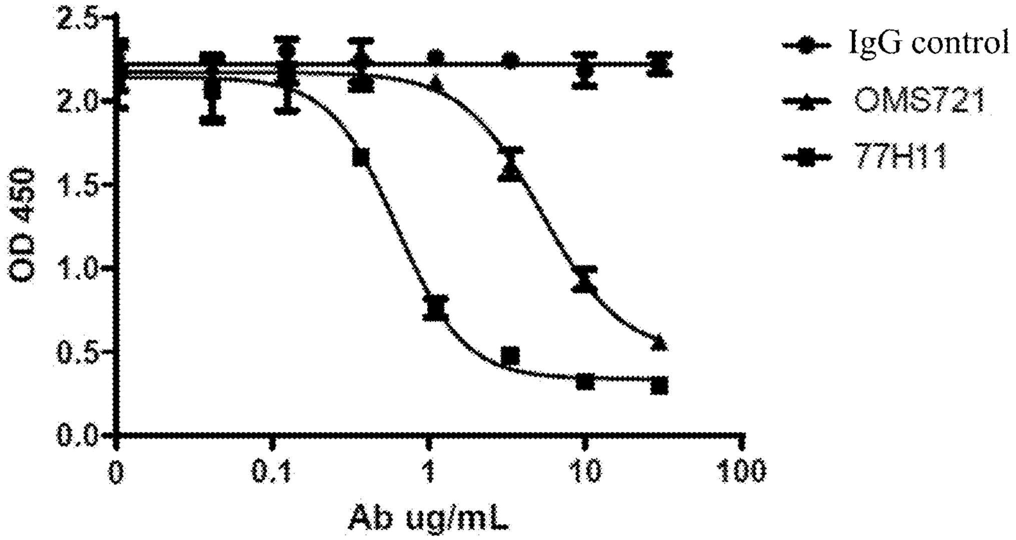
FIGS. 1A-1D show assay results for the activity of the anti-MASP2 antibodies 77H11, 29C1, 11165, 67D2, and 67E8 of the present disclosure for the lectin pathway in a 1% human serum, with an isotype control of hIgG4 used as a negative control and OMS721 used as a positive control.
Figure 1B:
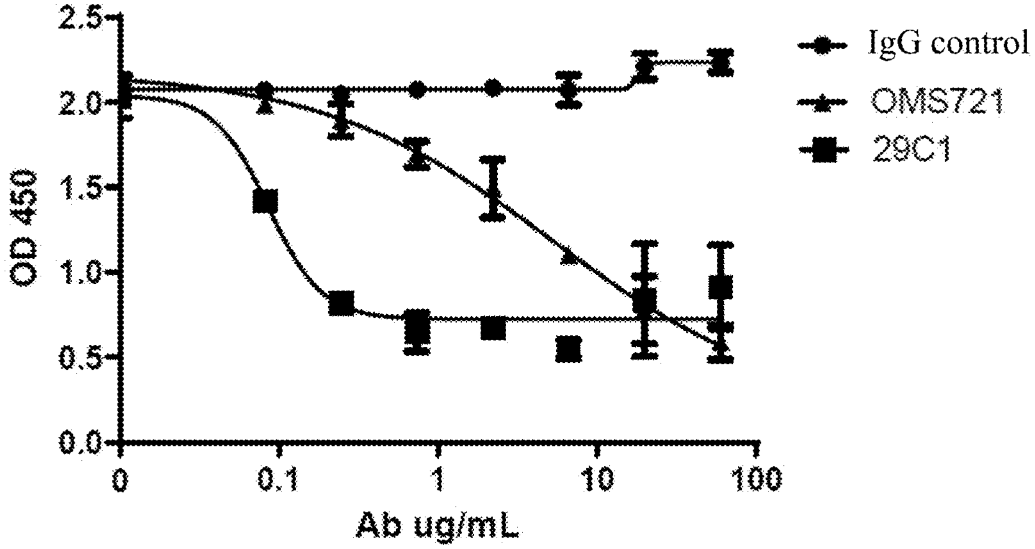
Figure 1C:
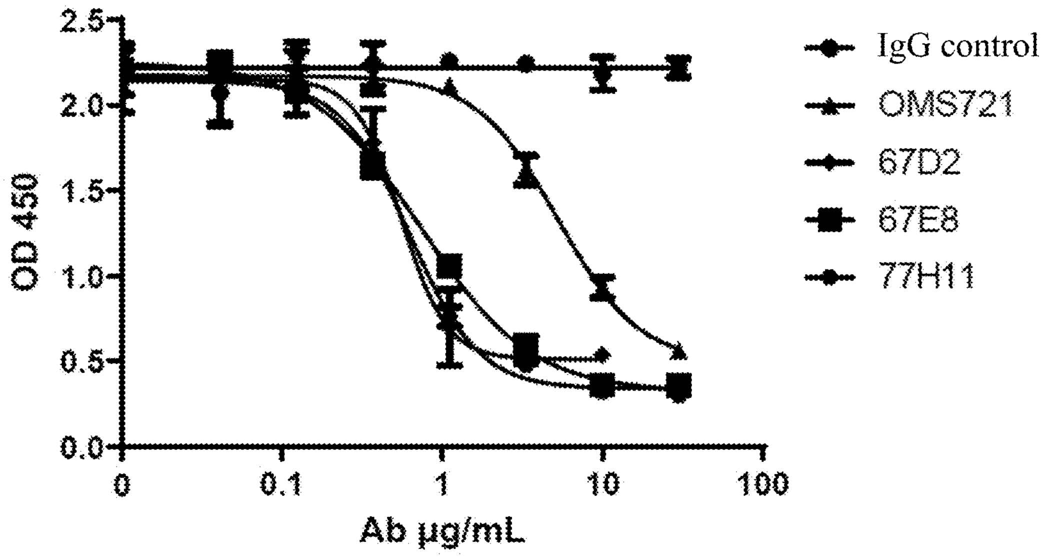
Figure 1D:
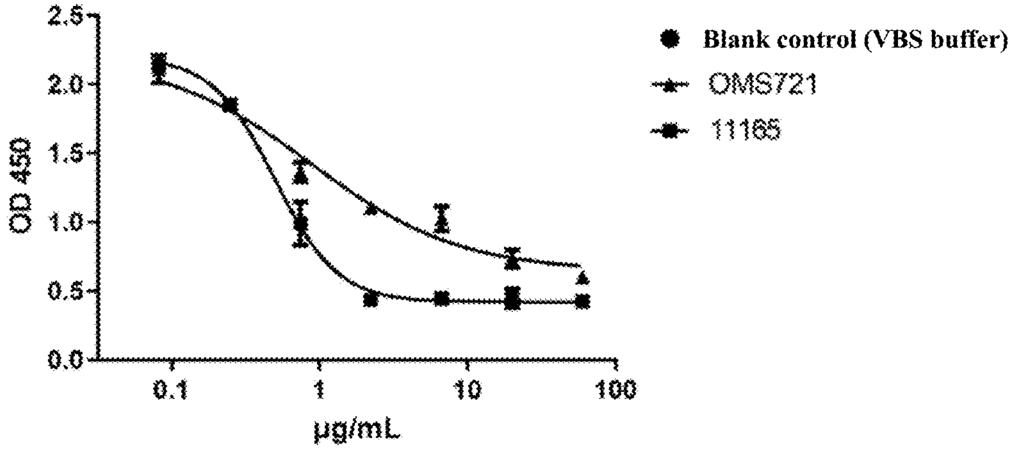

The present disclosure is further described below with reference to examples, but these examples are not intended to limit the scope of the present disclosure.

Experimental procedures without specific conditions indicated in the examples or test examples are generally conducted according to conventional conditions, or according to conditions recommended by the manufacturer of the starting materials or commercial products. See Sambrook et al., Molecular Cloning: A Laboratory Manual, Cold Spring Harbor Laboratory Press: Current Protocols in Molecular Biology, Ausubel et al., Greene Publishing Association, Wiley Interscience, NY. Reagents without specific origins indicated are commercially available conventional reagents.

Example 1. Preparation of MASP2 Recombinant Proteins

In order to prepare antigens for antibody screening, CHO-S stable cell strains of MASP2 mutant, which separately express recombinant proteins of human enzymatic mutant human MASP2A (S633A), murine enzymatic mutant murine MASP2A (S632A), and monkey enzymatic mutant monkey MASP2A (S633A) recombinant proteins, were prepared. MASP2 (S632A) or MASP2 (S633A) is an enzymatic mutant form of MASP2 (*J Biol Chem.* 2013; 288(13): 8922-8934), which aims to reduce the autocatalysis of the protein and improve the protein stability. Furthermore, in order to improve the yield during expression, the signal peptide was replaced, in which the original signal peptide MRLLTLLGLLCGSVA (SEQ ID NO: 60) (see Uniprot website) was replaced with MEFGLSWLFLVAILKGVQC (SEQ ID NO: 61), and position 663 or 662 was a position number based on natural counting in the original sequence. The cell strains were cultured, and the supernatants were collected. The recombinant proteins were obtained by purification by chromatography, with amino acid sequences shown as follows:

```
>Human MASP2A (S633A) protein:
                                                SEQ ID NO: 1
MEFGLSWLFLVAILKGVQCTPLGPKWPEPVFGRLASPGFPGEYANDQERRWTLTAPP

GYRLRLYFTHFDLELSHLCEYDFVKLSSGAKVLATLCGQESTDTERAPGKDTFYSLGS

SLDITFRSDYSNEKPFTGFEAFYAAEDIDECQVAPGEAPTCDHHCHNHLGGFYCSCRA

GYVLHRNKRTCSALCSGQVFTQRSGELSSPEYPRPYPKLSSCTYSISLEEGFSVILDFV

ESFDVETHPETLCPYDFLKIQTDREEHGPFCGKTLPHRIETKSNTVTITFVTDESGDHT

GWKIHYTSTAQPCPYPMAPPNGHVSPVQAKYILKDSFSIFCETGYELLQGHLPLKSFT

AVCQKDGSWDRPMPACSIVDCGPPDDLPSGRVEYITGPGVTTYKAVIQYSCEETFYT

MKVNDGKYVCEADGFWTSSKGEKSLPVCEPVCGLSARTTGGRIYGGQKAKPGDFP

WQVLILGGTTAAGALLYDNWVLTAAHAVYEQKHDASALDIRMGTLKRLSPHYTQA

WSEAVFIHEGYTHDAGFDNDIALIKLNNKVVINSNITPICLPRKEAESFMRTDDIGTAS

GWGLTQRGFLARNLMYVDIPIVDHQKCTAAYEKPPYPRGSVTANMLCAGLESGGKD

SCRGDAGGALVFLDSETERWFVGGIVSWGSMNCGEAGQYGVYTKVINYIPWIENIIS

DFGGSDYKDDDDKHHHHHH
(Note: the underlined part indicates a signal peptide, the
italicized part indicates a His tag, and the gray part indicates a
mutation at position 633 to A (S633A))
```

-continued

>Monkey MASP2A (S633A) protein:

SEQ ID NO: 2

MEFGLSWLFLVAILKGVQCTPLGPKWPEPVFGRLASPGFPGEYANDQERRWTLTAPP

GYRLRLYFTHFDLELSHLCEYDFVKLSSGAKVLATLCGHESTDTERAPGNDTFYSLGS

SLDITFRSDYSNEKPFTGFEAFYAAEDIDECQVAPGEAPACDHHCHNHLGGFYCSCRV

GYILHRNKRTCSALCSGQVFTQRSGELSSPEYPQPYPKLSSCTYSIRLEEGFSVILDFVE

SFDVETHPETLCPYDFLKIQIDSEEHGPFCGKTLPRRIETKSNTVTITFVTDESGDHTG

WKIHYTSTAQPCPYPMAPPNGHLSPVQAKYILKDSFSIFCEPGYELLQGHLPLKSFAA

VCQKDGSWDQPMPSCSIVDCGPPDDLPSGRVEYITGPEVTTYKAVIQYSCEETFYTM

KVNDGKYVCEADGFWTSSKGERSPPVCEPVCGLSARTTGGRIYGGQKAKPGDFPWQ

VLILGGSTAAGALLYDNWVLTAAHAIYEQKHDASSLDIRLGALKRLSPHYTQAWAEA

VFIHEGYTHDAGFDNDIALIKLNNKVVINSNITPICLPRKEAESFMRTDDIGTASGWGL

TQRGLLARNLMYVDIPIVDHQKCTAAYEKPPYSGGSVTANMLCAGLESGGKDSCRG

DAGGALVFLDNETQRWFVGGIVSWGSMNCGEAGQYGVYTKVINYIPWIKNIISNFGG

SDYKDDDDK*HHHHHH*

(Note: the underlined part indicates a signal peptide, the italicized part indicates a His tag, and the gray part indicates a mutation at position 633 to A (S633A))

>Murine MASP2A (S632A) protein:

SEQ ID NO: 3

MEFGLSWLFLVAILKGVQCTPLGSKWPEPVFGRLVSPGFPEKYADHQDRSWTLTAPP

GYRLRLYFTHFDLELSYRCEYDFVKLSSGTKVLATLCGQESTDTEQAPGNDTFYSLGP

SLKVTFHSDYSNEKPFTGFEAFYAAEDVDECRVSLGDSVPCDHYCHNYLGGYYCSCR

AGYVLHQNKHTCSALCSGQVFTGRSGYLSSPEYPQPYPKLSSCTYSIRLEDGFSVILD

FVESFDVETHPEAQCPYDSLKIQTDKGEHGPFCGKTLPPRIETDSHKVTITFATDESGN

HTGWKIHYTSTARPCPDPTAPPNGSISPVQAIYVLKDRFSVFCKTGFELLQGSVPLKSF

TAVCQKDGSWDRPMPECSIIDCGPPDDLPNGHVDYITGPEVTTYKAVIQYSCEETFYT

MSSNGKYVCEADGFWTSSKGEKLPPVCEPVCGLSTHTIGGRIVGGQPAKPGDFPWQ

VLLLGQTTAAAGALIHDNWVLTAAHAVYEKRMAASSLNIRMGILKRLSPHYTQAWP

EEIFIHEGYTHGAGFDNDIALIKLKNKVTINGSIMPVCLPRKEAASLMRTDFTGTVAG

WGLTQKGLLARNLMFVDIPIADHQKCTAVYEKLYPGVRVSANMLCAGLETGGKDSC

RGDAGGALVFLDNETQRWFVGGIVSWGSINCGAADQYGVYTKVINYIPWIENIISNF

GGSDYKDDDDK*HHHHHH*

(Note: the underlined part indicates a signal peptide, the italicized part indicates a His tag, and the gray partindicates a mutation at position 632 to A (S632A))

In order to identify antigen-binding sites of antibodies, different fragments of human MASP2 were prepared, including human MASP2 CCP1, human MASP2 CCP1-CCP2-SP (S633A), and human MASP2 CCP2-SP (S633A). CCP1-CCP2-SP (S633A) and CCP2-SP (S633A) were prepared by transforming an *Escherichia coli* BL21 strain with plasmids, isolating and purifying proteins, and performing denaturation and renaturation; CCP1 was prepared by transiently transfecting CHO cells, and expressing and isolating proteins. The amino acid sequences of the MASP2 protein fragments are as follows:

```
>CCP1-CCP2-SP (S633A):
                                                    SEQ ID NO: 4
MGSSHHHHHHSSGLVPRGSHMTGWKIHYTSTAQPCPYPMAPPNGHVSPVQAKYILK

DSFSIFCETGYELLQGHLPLKSFTAVCQKDGSWDRPMPACSIVDCGPPDDLPSGRVEY

ITGPGVTTYKAVIQYSCEETFYTMKVNDGKYVCEADGFWTSSKGEKSLPVCEPVCG

LSARTTGGRIYGGQKAKPGDFPWQVLILGGTTAAGALLYDNWVLTAAHAVYEQKH

DASALDIRMGTLKRLSPHYTQAWSEAVFIHEGYTHDAGFDNDIALIKLNNKVVINSNI

TPICLPRKEAESFMRTDDIGTASGWGLTQRGFLARNLMYVDIPIVDHQKCTAAYEKP

PYPRGSVTANMLCAGLESGGKDSCRGDAGGALVFLDSETERWFVGGIVSWGSMNC

GEAGQYGVYTKVINYIPWIENIISDF

>CCP2-SP (S633A):
                                                    SEQ ID NO: 5
MGSSHHHHHHSSGLVPRGSHMIVDCGPPDDLPSGRVEYITGPGVTTYKAVIQYSCEE

TFYTMKVNDGKYVCEADGFWTSSKGEKSLPVCEPVCGLSARTTGGRIYGGQKAKPG

DFPWQVLILGGTTAAGALLYDNWVLTAAHAVYEQKHDASALDIRMGTLKRLSPHY

TQAWSEAVFIHEGYTHDAGFDNDIALIKLNNKVVINSNITPICLPRKEAESFMRTDDIG

TASGWGLTQRGFLARNLMYVDIPIVDHQKCTAAYEKPPYPRGSVTANMLCAGLESG

GKDSCRGDAGGALVFLDSETERWFVGGIVSWGSMNCGEAGQYGVYTKVINYIPWIE

NIISDF
(Note: the gray part indicates a mutation at position 633 to A (S633A))

>CCP1:
                                                    SEQ ID NO: 6
MDAMKRGLCCVLLLCGAVFVSPSYTSTAHACPYPMAPPNGHVSPVQAKYILKDSFSI

FCETGYELLQGHLPLKSFTAVCQKDGSWDRPMPACSAHHHHHHHHHH
```

Example 2. Screening and Preparation of Anti-MASP2 Antibodies

MASP2-specific antibodies were screened and performed by mouse immunization and phage display.

1. Mouse Immunization:

Balb/c mice were immunized with the human MASP2A protein prepared in Example 1 as an antigen, and the mice with the highest titer were selected for hybridoma cell fusion. Hybridoma cell fusion and culture: myeloma cells passaged 24 h before were taken from 3 culture dishes (10 cm), washed once with an RPMI-1640 medium without HEPES, and resuspended, and 2-4×10$^7$ cells were obtained after counting. After 72 h of immunization, the mice were sacrificed. The spleens were taken aseptically, washed with an RPMI-1640 culture medium without HEPES, cut into pieces, and ground to obtain spleen cells. The spleen cells were pipetted, filtered, centrifuged at 1000 rpm for 5 min, and resuspended, and 1-2×10$^8$ were obtained after counting. Myeloma cells and spleen cells were mixed well and centrifuged at 1000 rpm for 5 min. The supernatant was discarded, and the precipitate was dispersed and preheated in a water bath at 40° ° C. 1 mL of PEG preheated to 40° C. was added dropwise to the centrifuge tube over 60 s with gentle stirring. The mixture was gently stirred for 1 min. 1 mL of medium was added over 30 s, 3 mL of medium was added over 1 min, and 16 mL of medium was added over 1 min. The mixture was left to stand for 10 min and centrifuged at 1000 rpm for 5 min. The supernatant was discarded, and the cells were resuspended in an HAT-OPI medium (an RPMI-1640 medium containing 20% FBS, 1×HAT, and 1×OPI), and incubated at 37° ° C. with 5% $CO_2$. On day 5 after the fusion, 20% FBS in RPMI-1640 medium (containing 2×HAT and 1×OPI) was added at 50 μL/well. On days 7-10 after the fusion, a complete medium change was performed with an HAT-OPI culture medium. On days 10-14 after the fusion, an ELISA assay was performed on human MASP2 and monkey MASP2 proteins according to cell growth density, and positive clones were selected.

The ELISA assay was performed as follows: A plate was coated with 1 μg/mL antigen overnight at 4° C. at 50 μL/well. The plate was washed 3 times with PBS and then blocked with PBS containing 3% BSA at room temperature for 1 h. The plate was washed 3 times with PBST. A hybridoma cell supernatant was added, and the mixture was incubated at room temperature for 1 h. The plate was washed 3 times with PBST, and then washed 3 times with PBS. A secondary antibody (1:2000; invitrogen, goat anti-mouse IgG (H+L) secondary antibody, 31430) was added, and the mixture was incubated at room temperature for 1 h. The plate was washed 3 times with PBST, and then washed 3 times with PBS. A TMB substrate was added, and the mixture was incubated at room temperature for 10 min. Then, the reaction was stopped, and a signal value (light absorption value at 450 nm) was read.

2. Phage Display

An immunoadsorption plate was coated with a human MASP2A antigen and incubated with a phage antibody synthesis library for solid-phase screening. After three rounds of panning, human MASP2- and monkey MASP2-positive phages were obtained.

The phage display screening for positive clones was performed as follows: An immunotube was coated with 4 mL of MASP2A (5 ng/μL) and incubated at 4° C. overnight.

The fully human phage library was blocked with 5% BSA/PBS at room temperature for 1 h. The phage library was transferred to the immunotube coated with MASP2A, incubated in a rotary shaker at room temperature for 1 h, washed 5 times with PBS, eluted with 1000 μL of TEA, and neutralized by addition of 400 μL of Tris-HCl (pH 7.4). 10 mL of TGI (OD value of 0.4) was added for infection, and the mixture was incubated at 37° C. for 40 min. Output was measured, and the mixture was applied to an Amp+ plate and incubated at 30° C. overnight. The bacteria were scraped, seeded into 50 mL of 2× TY medium (with Amp and 1% glucose) until the OD value reached 0.1, and incubated by shaking at 200 rpm for 80 min at 37° C. until the OD value reached 0.4-0.6. 10 mL of the suspension was taken, and 500 μL of the helper phage M13KO7 was added for infection at 37° C. for 40 min. The mixture was centrifuged, and the supernatant was removed. The precipitate was resuspended in 100 mL of 2× TY medium (with Amp and Kana) and incubated by shaking at 200 rpm overnight at 30° C. The suspension was centrifuged at 4000 rpm for 30 min, and the supernatant was collected. 10 mL of PEG/NaCl was added, and the mixture was precipitated on ice for 1 h and centrifuged at 4000 rpm for 30 min. 1 mL of PBS was added to the precipitate for resuspension. The suspension was centrifuged at 13,000 rpm for 3 min, and the precipitate was removed. The phages were resuspended in PBS and subjected to the next round of panning. Monoclonals were seeded into a 96-well plate and incubated by shaking at 220 rpm for 3 h at 37° C. 1 mM IPTG was added for induction at 30° C. overnight. Meanwhile, the 96-well plate was coated with MASP2 at a concentration of 2 ng/μL at 50 μL/well, and incubated at 4° C. overnight. The next day, after the ELISA plate was washed once, 200 μL of 2% MPBS was added to block the ELISA plate at 37° C. for 1 h. The bacterial solution cultured overnight was centrifuged at 4000 g for 10 min, and the supernatant was transferred to a new 96-well plate. After the ELISA plate was washed twice, 25 μL of 2% MPBS blocking solution was added, followed by 25 μL of culture supernatant. The mixture was mixed well, and incubated at 25° C. for 1 h. After the ELISA plate was washed 3 times, 100 μL of anti-Fab-HRP antibody (1:5000 in 2% MPBS) was added, and the mixture was incubated at 25° C. for 1 h. After the ELISA plate was washed 4 times, color development was performed. The positive clones were obtained by the ELISA assay.

By two methods of mouse immunization with antigenic proteins and phage display screening, positive clones were obtained, and after sequencing and purification, the anti-MASP2 antibodies were obtained, with amino acid sequences of the heavy chain variable region (VH) and the light chain variable region (VL) shown as follows (the underlined parts indicate CDRs of the heavy chain variable region or the light chain variable region):

>77H11 VH:

SEQ ID NO: 7

DVQLQESGPGLVKPSQSLSLTCTVTGYSITSDYAWNWIRQFPGNKLEWMGYISYSGR

TSYNPSLKSRISITRDTSKNQFFLQLNSVTTEDTATYYCAVLYALDYWGQGTSVTVSS

>77H11 VL:

SEQ ID NO: 8

DIVMTQSQKFMSTSVGDRVSVTCKASQNVDTNVAWYQQKPGQSPKALIYSASYRYS

GVPDRFTGSGSGTDFTLTISDVQSEDLAEYFCQQYNSNPLTFGSGTKLEIK

>67D2 VH:

SEQ ID NO: 9

DVQLQESGPGLVKPSQSLSLTCTVTGYSITSDYAWNWIRQFPGNKLEWMGYISYSGR

TSYNPSLKSRISITRDTSKNQFFLQLNSVTTEDTATYYCAILYAMNFWGQGTSVTVSS

>67D2 VL:

SEQ ID NO: 10

DIVMTQSQKFMSTSVGDRVSVTCKASQNVDTNVAWYQQKPGQSPKALIYSASYRFS

GVPDRFTGSGSGTDFTLTISNVQSEDLAEYFCQQYNSNPLTFGSGTKLEIK

>67E8 VH:

SEQ ID NO: 11

DVQLQESGPGLVKPSQSLSLTCTVTGYSITSDYAWNWIRQFPGNKLEWMGYISYSGR

TSYNPSLKSRISITRDTSKNQFFLQLNSVTTEDTATYYCAILYAMDYWGQGTSVTVSS

>67E8 VL:

SEQ ID NO: 12

DIVMTQSQKFMSTSVGDRVSVTCKASQNVDTNVAWYQQKPGQSPKALIYSASYRYS

GVPDRFTGSGSGTDFTLTISNVQSEDLAEYFCQQYNSNPLTFGSGTKLEIK

>29C1 VH:

SEQ ID NO: 13

EVQLVESGGGLVKPGGSLKLSCAASGFTFSRFALSWVRQTPEKRLEWVAAVSRGGDY

TYYPDSMKGRFTISRDNAMNTLYLQMSSLSSEDTAMYYCARHLYGYGHYYAMDYW

GQGTSVTVSS

-continued

>29C1 VL:

SEQ ID NO: 14

DIVMTQSHKFMSTSVGDRVSITCKASQDVNTAVAWYQQKPGQSPKLLIYSASYRYTG

VPDRFTGSGSGTDFTFTISSVQAEDLAVYYCQQHYSTPYTFGGGTKLEIK

>11165 VH:

SEQ ID NO: 15

QVQLQESGPGLVKPSETLSLTCTVSGGSISSGEYFWGWIRQPPGKGLEWIGSIYYSGST

YYNPSLKSRVTISVDTSKNQFSLKLSSVTAADTAVYYCARSLKAARRDAFDIWGQGT

TVTVSS

>11165 VL:

SEQ ID NO: 16

QSVLTQPPSVSVSPGQTASITCSGHKLGDKYAYWYQQKPGQSPVLVIYQDTKRPSGIP

ERFSGFNSGNTATLTISGTQATDEADYYCQTWDSSTGVFGAGTKVTVL

TABLE 1

CDR sequences of anti-MASP2 antibodies (Kabat numbering scheme)

| Antibody No. | | Heavy chain variable region | | Light chain variable region |
|---|---|---|---|---|
| 77H11 | HCDR1 | SDYAWN (SEQ ID NO: 17) | LCDR1 | KASQNVDTNVA (SEQ ID NO: 20) |
| | HCDR2 | YISYSGRTSYNPSLKS (SEQ ID NO: 18) | LCDR2 | SASYRYS (SEQ ID NO: 21) |
| | HCDR3 | LYALDY (SEQ ID NO: 19) | LCDR3 | QQYNSNPLT (SEQ ID NO: 22) |
| 67D2 | HCDR1 | SEQ ID NO: 17 | LCDR1 | SEQ ID NO: 20 |
| | HCDR2 | SEQ ID NO: 18 | LCDR2 | SASYRFS (SEQ ID NO: 24) |
| | HCDR3 | LYAMNF (SEQ ID NO: 23) | LCDR3 | SEQ ID NO: 22 |
| 67E8 | HCDR1 | SEQ ID NO: 17 | LCDR1 | SEQ ID NO: 20 |
| | HCDR2 | SEQ ID NO: 18 | LCDR2 | SEQ ID NO: 21 |
| | HCDR3 | LYAMDY (SEQ ID NO: 25) | LCDR3 | SEQ ID NO: 22 |
| 29C1 | HCDR1 | RFALS (SEQ ID NO: 28) | LCDR1 | KASQDVNTAVA (SEQ ID NO: 31) |
| | HCDR2 | AVSRGGDYTYYPDSMKG (SEQ ID NO: 29) | LCDR2 | SASYRYT (SEQ ID NO: 32) |
| | HCDR3 | HLYGYGHYYAMDY (SEQ ID NO: 30) | LCDR3 | QQHYSTPYT (SEQ ID NO: 33) |
| 11165 | HCDR1 | SGEYFWG (SEQ ID NO: 34) | LCDR1 | SGHKLGDKYAY (SEQ ID NO: 37) |
| | HCDR2 | SIYYSGSTYYNPSLKS (SEQ ID NO: 35) | LCDR2 | QDTKRPS (SEQ ID NO: 38) |
| | HCDR3 | SLKAARRDAFDI (SEQ ID NO: 36) | LCDR3 | QTWDSSTGV (SEQ ID NO: 39) |

77H11, 67D2, and 67E8 have the following CDRs:
HCDR1: SDYAWN (SEQ ID NO: 17);
HCDR2: YISYSGRTSYNPSLKS (SEQ ID NO: 18);
HCDR3: LYA$X_1X_2X_3$ (SEQ ID NO: 26), wherein, $X_1$ is selected from the group consisting of L and M, $X_2$ is selected from the group consisting of D and N, and $X_3$ is selected from the group consisting of Y and F;
LCDR1: KASQNVDTNVA (SEQ ID NO: 20);
LCDR2: SASYR$X_4$S (SEQ ID NO: 27), wherein, $X_4$ is selected from the group consisting of Y and F;
LCDR3: QQYNSNPLT (SEQ ID NO: 22).

Example 3. Identification of Inhibition of Lectin Pathway Activity by Anti-MASP2 Antibodies The functional validation was performed on the obtained anti-MASP2 antibodies for in vitro inhibition of the lectin pathway activity with 1% human serum.

The identification of the functional activity of the antibodies in 1% human serum was performed as follows: A 384-well plate was coated with 50 μg/mL mannan solution at 25 μL/well and incubated at 4° C. overnight. The plate was washed 4 times with TBST at 50 μL/well, blocked with a 3% BSA blocking solution (solvent: TBS) at 50 μL/well, and incubated at room temperature for 2 h. The plate was washed 4 times with TBST at 50 μL/well. The anti-MASP2 antibody at a corresponding concentration was mixed with 1% human serum. The mixture was incubated at 4° ° C. for 1 h and added to the above 384-well plate at 15 μL/well. The mixture was incubated at 37° C. for 1 h. The plate was washed 4 times with TBST at 50 μL/well. A primary antibody (biotin-human Anti-C4c, Agrisera #IMSO1-031-305) diluted with 0.5% BSA was added at 15 μL/well. The mixture was centrifuged at 800 g/min and incubated at room temperature for 1 h. The plate was washed 4 times again with TBST at 50 μL/well. A secondary antibody (SA-HRP) diluted in a 1:5000 ratio with a 0.5% BSA solution was added at 15 μL/well. The mixture was incubated at room temperature for 30 min. The plate was washed 4 times again with TBST at 50 μL/well. A TMB chromogenic solution was added at 45 μL/well. The mixture was incubated at room temperature for 15 min in the dark. Finally, a stop solution was added at 45 μL/well, and OD450 values were determined.

A positive control antibody OMS721 was synthesized according to WO2012151481A, with sequences shown as follows:

```
>Full-length heavy chain of OMS721:
                                              SEQ ID NO: 40
QVTLKESGPVLVKPTETLTLTCTVSGFSLSRGKMGVSWIRQPPGKALEWLAHIFSSDE

KSYRTSLKSRLTISKDTSKNQVVLTMTNMDPVDTATYYCARIRRGGIDYWGQGTLV

TVSSASTKGPSVFPLAPCSRSTSESTAALGCLVKDYFPEPVTVSWNSGALTSGVHTFP

AVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

>Full-length light chain of OMS721:
                                              SEQ ID NO: 41
QPVLTQPPSLSVSPGQTASITCSGEKLGDKYAYWYQQKPGQSPVLVMYQDKQRPSGI

PERFSGSNSGNTATLTISGTQAMDEADYYCQAWDSSTAVFGGGTKLTVLGQPKAAP

SVTLFPPSSEELQANKATLVCLISDFYPGAVTVAWKADSSPVKAGVETTTPSKQSNN

KYAASSYLSLTPEQWKSHRSYSCQVTHEGSTVEKTVAPTECS
```

As shown in FIGS. 1A-1D and Tables 2-4, the results showed that 77H11, 67D2, 67E8, 29C1, and 11165 were all able to significantly inhibit the lectin pathway, with the potency superior to that of the positive control OMS721. The antibodies 77H11, 67D2, 67E8, 29C1, and 11165 here were all full-length anti-MASP2 antibodies constructed by connecting an antibody heavy chain variable region with a human IgG4 heavy chain Fc region, wherein the human IgG4 heavy chain Fc was set forth in SEQ ID NO: 53. The hIgG4 used was an isotype control.

TABLE 2

Inhibitory effect of the anti-MASP2 antibodies on the lectin pathway in a 1% human serum

| Antibody | $IC_{50}$ (μg/mL) |
|---|---|
| OMS721 | 5.278 |
| 77H11 | 0.630 |
| 67D2 | 0.559 |
| 67E8 | 0.738 |

TABLE 3

Inhibitory effect of the anti-MASP2 antibodies on the lectin pathway in a 1% human serum

| Antibody | $IC_{50}$ (μg/mL) |
|---|---|
| OMS721 | 2.858 |
| 29C1 | 0.086 |

TABLE 4

Inhibitory effect of the anti-MASP2 antibodies on the lectin pathway in a 1% human serum

| Antibody | $IC_{50}$ (μg/mL) |
|---|---|
| OMS721 | 0.885 |
| 11165 | 0.499 |

Example 4. Humanization of Anti-MASP2 Antibodies

The anti-MASP2 antibodies 29C1 and 77H11 were selected for humanization, followed by activity identification in human serum.

For 29C1, IGKV1-33*01 was used as a humanization template for the light chain, and IGKV3-21*01 was used as a humanization template for the heavy chain. Both chains were subjected to several back mutations. The sequences were combined to obtain 6 molecules, with humanized sequences shown as follows (the underlined parts indicate the heavy or light chain CDRs):

```
>29C1 H1:
                                        SEQ ID NO: 42
EVQLVESGGGLVKPGGSLRLSCAASGFTFSRFALSWVRQAPGKGLEWVS

AVSRGGDYTYYPDSMKGRFTISRDNAKNSLYLQMNSLRAEDTAVYYCAR

HLYGYGHYYAMDYWGQGTTVTVSS

>29C1 H2:
                                        SEQ ID NO: 43
EVQLVESGGGLVKPGGSLRLSCAASGFTFSRFALSWVRQAPGKGLEWVA

AVSRGGDYTYYPDSMKGRFTISRDNAKNSLYLQMNSLRAEDTAVYYCAR

HLYGYGHYYAMDYWGQGTTVTVSS

>29C1 H3:
                                        SEQ ID NO: 44
EVQLVESGGGLVKPGGSLRLSCAASGFTFSRFALSWVRQAPGKGLEWVA

AVSRGGDYTYYPDSMKGRFTISRDNAKNSLYLQMNSLRAEDTAVYYCAR

HLYGYGHYYAMDYWGQGTTVTVSS

>29C1 L1:
                                        SEQ ID NO: 45
DIQMTQSPSSLSASVGDRVTITCKASQDVNTAVAWYQQKPGKAPKLLIY

SASYRYTGVPSRFSGSGSGTDFTFTISSLQPEDIATYYCQQHYSTPYTF

GGGTKVEIK

>29C1 L2:
                                        SEQ ID NO: 46
DIVMTQSPSSLSASVGDRVTITCKASQDVNTAVAWYQQKPGKSPKLLIY

SASYRYTGVPSRFSGSGSGTDFTFTISSLQPEDIATYYCQQHYSTPYTF

GGGTKVEIK
```

For 77H11, IGKV1-27*01 was used as a humanization template for the light chain, and IGKV4-30-4*01 was used as a humanization template for the heavy chain. Both chains were subjected to several back mutations. The sequences were combined to obtain 8 molecules, with humanized sequences shown as follows (the underlined parts indicate the heavy or light chain CDRs):

```
>77H11 H1:
                                        SEQ ID NO: 47
EVQLQESGPGLVKPSQTLSLTCTVSGGSISSDYAWNWIRQPPGKGLEWI

GYISYSGRTSYNPSLKSRVTISVDTSKNQFSLKLSSVTAADTAVYYCAV

LYALDYWGQGTTVTVSS

>77H11 H2:
                                        SEQ ID NO: 48
EVQLQESGPGLVKPSQTLSLTCTVSGYSITSDYAWNWIRQPPGKGLEWI

GYISYSGRTSYNPSLKSRVTISVDTSKNQFSLKLSSVTAADTAVYYCAV

LYALDYWGQGTTVTVSS

>77H11 H3:
                                        SEQ ID NO: 49
EVQLQESGPGLVKPSQTLSLTCTVSGYSITSDYAWNWIRQPPGKGLEWI

GYISYSGRTSYNPSLKSRVTISRDTSKNQFSLKLSSVTAADTAVYYCAV

LYALDYWGQGTTVTVSS
```

-continued

```
>77H11 H4:
                                        SEQ ID NO: 50
EVQLQESGPGLVKPSQTLSLTCTVSGYSITSDYAWNWIRQPPGNKLEWM

GYISYSGRTSYNPSLKSRITISRDTSKNQFSLKLSSVTAADTAVYYCAV

LYALDYWGQGTTVTVSS

>77H11 L1:
                                        SEQ ID NO: 51
DIQMTQSPSSLSASVGDRVTITCKASQNVDTNVAWYQQKPGKVPKALIY

SASYRYSGVPSRFSGSGSGTDFTLTISSLQPEDVATYYCQQYNSNPLTF

GQGTKLEIK

>77H11 L2:
                                        SEQ ID NO: 52
DIQMTQSPSSLSASVGDRVTITCKASQNVDTNVAWYQQKPGKSPKALIY

SASYRYSGVPSRFSGSGSGTDFTLTISSLQPEDVAEYYCQQYNSNPLTF

GQGTKLEIK
```

The sequences of the humanized anti-MASP2 antibodies are shown in Table 5.

TABLE 5

Heavy chain variable regions and light chain variable regions of the anti-MASP2 antibodies

| Antibody No. | Heavy chain variable region | Light chain variable region |
|---|---|---|
| 29C1(H1L1) | SEQ ID NO: 42 | SEQ ID NO: 45 |
| 29C1(H2L1) | SEQ ID NO: 43 | |
| 29C1(H3L1) | SEQ ID NO: 44 | |
| 29C1(H1L2) | SEQ ID NO: 42 | SEQ ID NO: 46 |
| 29C1(H2L2) | SEQ ID NO: 43 | |
| 29C1(H3L2) | SEQ ID NO: 44 | |
| 77H1(H3L1) | SEQ ID NO: 49 | SEQ ID NO: 51 |
| 77H1(H4L1) | SEQ ID NO: 50 | |
| 77H1(H2L2) | SEQ ID NO: 48 | SEQ ID NO: 52 |
| 77H1(H3L2) | SEQ ID NO: 49 | |
| 77H1(H4L2) | SEQ ID NO: 50 | |
| 77H1(H1L1) | SEQ ID NO: 47 | SEQ ID NO: 51 |
| 77H1(H1L2) | | SEQ ID NO: 52 |

The antibodies in Table 5 were all full-length anti-MASP2 antibodies constructed by connecting an antibody heavy chain variable region with a human IgG4 heavy chain Fc region. The heavy chain Fc region comprised a hinge region, was a human IgG4 Fc region with an S228P mutation, and had a sequence set forth in SEQ ID NO: 53. The S228P was numbered according to the EU numbering scheme.

```
>Human IgG4 Fc (S228P):
                                        SEQ ID NO: 53
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK
```

Exemplary full-length heavy chains and full-length light chains of the anti-MASP2 antibodies are shown as follows:

>Full-length heavy chain of 29C1 (H1L1):

SEQ ID NO: 54

EVQLVESGGGLVKPGGSLRLSCAASGFTFSRFALSWVRQAPGKGLEWVSAVSRGGD

YTYYPDSMKGRFTISRDNAKNSLYLQMNSLRAEDTAVYYCARHLYGYGHYYAMDY

WGQGTTVTVSSASTKGPSVFPLAPCSRSTSESTAALGCLVKDYFPEPVTVSWNSGALT

SGVHTFPAVLQSSGLYSLSSVVTVPSSSLGTKTYTCNVDHKPSNTKVDKRVESKYGPP

CPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

>Full-length light chain of 29C1 (H1L1):

SEQ ID NO: 55

DIQMTQSPSSLSASVGDRVTITCKASQDVNTAVAWYQQKPGKAPKLLIYSASYRYTG

VPSRFSGSGSGTDFTFTISSLQPEDIATYYCQQHYSTPYTFGGGTKVEIK

RTVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

>Full-length heavy chain of 77H11 (H3L1):

SEQ ID NO: 56

EVQLQESGPGLVKPSQTLSLTCTVSGYSITSDYAWNWIRQPPGKGLEWIGYISYSGRTS

YNPSLKSRVTISRDTSKNQFSLKLSSVTAADTAVYYCAVLYALDYWGQGTTVTVSSAS

TKGPSVFPLAPCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRL

TVDKSRWQEGNVFSCSVMHEALHNHYTQKSLSLSLGK

>Full-length light chain of 77H11 (H3L1):

SEQ ID NO: 57

DIQMTQSPSSLSASVGDRVTITCKASQNVDTNVAWYQQKPGKVPKALIYSASYRYSG

VPSRFSGSGSGTDFTLTISSLQPEDVATYYCQQYNSNPLTFGQGTKLEIK

RTVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

Full-length sequences of 11165 are shown as follows:

>Full-length heavy chain of 11165:

SEQ ID NO: 58

QVQLQESGPGLVKPSETLSLTCTVSGGSISSGEYFWGWIRQPPGKGLEWIGSIYYSGST

YYNPSLKSRVTISVDTSKNQFSLKLSSVTAADTAVYYCARSLKAARRDAFDIWGQGT

TVTVSSASTKGPSVFPLAPCSRSTSESTAALGCLVKDYFPEPVTVSWNSGALTSGVHT

FPAVLQSSGLYSLSSVVTVPSSSLGTKTYTCNVDHKPSNTKVDKRVESKYGPPCPPCP

APEFLGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

-continued

```
>Full-length light chain of 11165:
                                                    SEQ ID NO: 59
QSVLTQPPSVSVSPGQTASITCSGHKLGDKYAYWYQQKPGQSPVLVIYQDTKRPSGIP

ERFSGFNSGNTATLTISGTQATDEADYYCQTWDSSTGVFGAGTKVTVL

GQPKANPTVTLFPPSSEELQANKATLVCLISDFYPGAVTVAWKADGSPVKAGVETTKP

SKQSNNKYAASSYLSLTPEQWKSHRSYSCQVTHEGSTVEKTVAPTECS
```

The antibodies were expressed and purified by conventional methods. The assay was performed and the full-length antibodies of the present disclosure were obtained.

The humanized antibodies described above were identified in a 90% human serum, which was closer to in vivo conditions, for their effects on the lectin pathway activity. The identification of the functional activity of the antibodies in a 90% human serum was performed as follows: A 384-well plate was coated with a sodium carbonate-sodium bicarbonate buffer (pH>9) containing 5 μg/mL mannan solution at 25 μL/well and incubated at 4° C. overnight. The plate was washed 3 times with TBST with 5 mM $Ca^{2+}$ at 50 μL/well. The plate was blocked with a 3% BSA blocking solution (solvent: TBS, 5 mM $Ca^{2+}$ was added) at 50 μL/well at room temperature for 1.5-2 h. The plate was washed 3 times with TBST at 50 μL/well, once with TBS at 50 μL/well, and once with VBS at 50 μL/well. The MASP2 antibody was diluted with VBS and mixed with human serum at a ratio of 1:9 (i.e., 90% human serum) to obtain a mixture. The mixture was incubated at 4° C. for 30 min and added to the above 384-well plate at 15 μL/well. The mixture was incubated at 4° C. for 1 h. The plate was washed 3 times with TBST at 50 μL/well. A primary antibody diluted with TBS with 0.5% BSA (Biotin-Chicken Anti-C4C, 6 g/mL) was added at 15 μL/well. The mixture was incubated at room temperature for 60 min. The plate was washed 3 times with TBST at 50 μL/well. A secondary antibody (SA-HRP) diluted in a 1:5000 ratio with a 0.5% BSA solution was added at 15 μL/well. The mixture was incubated at room temperature for 30 min. The plate was washed 3 times again with TBST at 50 μL/well. A TMB chromogenic solution was added at 45 μL/well. The mixture was incubated at room temperature for 15 min in the dark. Finally, a stop solution was added at 45 μL/well, and OD450 values were determined.

Figure 2A:
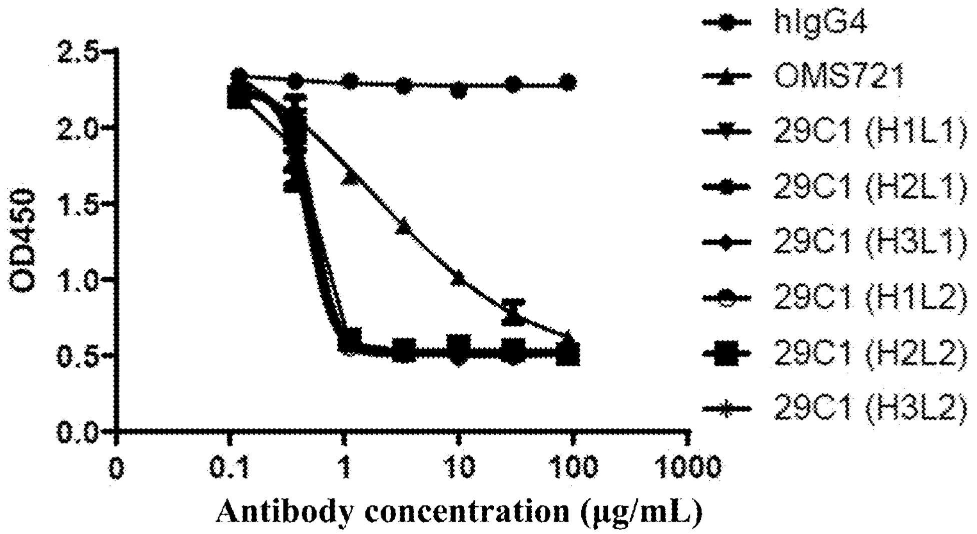
FIGS. 2A-2B are graphs showing assay results for the inhibition of the lectin pathway activity by the humanized antibodies 77H11 and 29C1 of the present disclosure in a 90% human serum, with an isotype control of hIgG4 used as a negative control and OMS721 used as a positive control.
Figure 2B:
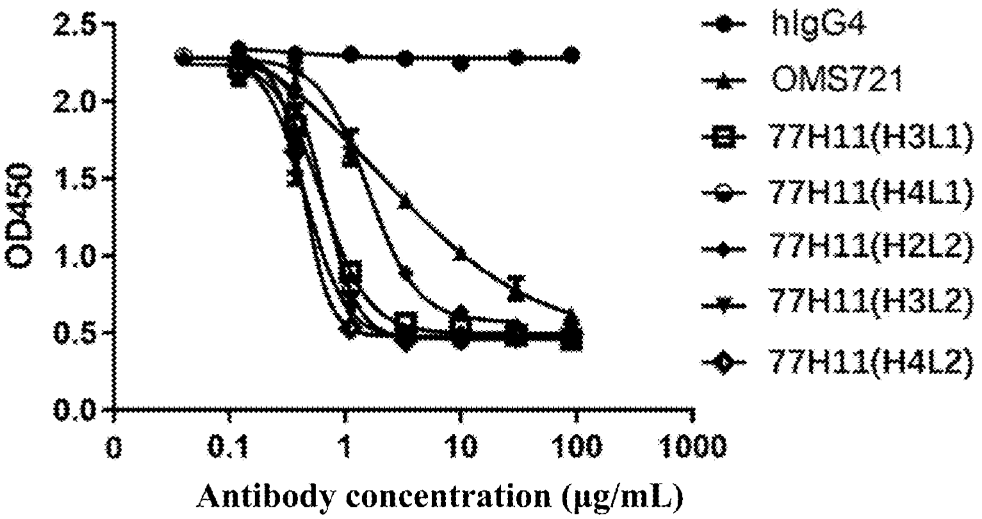

As shown in FIGS. 2A and 2B and Table 6, the humanized molecules 29C1 and 77H11 were both able to significantly inhibit the lectin pathway activity in a 90% human serum, with the potency superior to that of OMS721. The series of antibodies 29C1 and 77H11 were all full-length anti-MASP2 antibodies constructed by connecting an antibody heavy chain variable region with a human IgG4 heavy chain Fc region, wherein the human IgG4 heavy chain Fc was set forth in SEQ ID NO: 53. The hIgG4 used was an isotype control.

TABLE 6

Inhibitory effect of the anti-MASP2 antibodies on the lectin pathway in a 90% human serum

| Antibody | $IC_{50}$ (μg/mL) |
|---|---|
| OMS721 | 1.827 |
| 29C1 (H1L1) | 0.477 |
| 29C1 (H2L1) | 0.471 |
| 29C1 (H3L1) | 0.526 |

TABLE 6-continued

Inhibitory effect of the anti-MASP2 antibodies on the lectin pathway in a 90% human serum

| Antibody | $IC_{50}$ (μg/mL) |
|---|---|
| 29C1 (H1L2) | 0.534 |
| 29C1 (H2L2) | 0.555 |
| 29C1 (H3L2) | 0.515 |
| 77H11 (H3L1) | 0.624 |
| 77H11 (H4L1) | 0.670 |
| 77H11 (H2L2) | 1.578 |
| 77H11 (H3L2) | 0.454 |
| 77H11 (H4L2) | 0.443 |
| hIgG4 | No activity |
| | / |

Example 5. Determination of Affinity of Anti-MASP2 Antibodies

The binding properties of the anti-MASP2 antibodies were determined by the method of Biacore. The affinities of three antibody molecules, 29C1 (HIL1), 77H11 (H3L1) and 11165, for human MASP2, murine MASP2, and monkey MASP2 proteins were determined using a Biacore 8K (GE) instrument, with an isotype IgG antibody used as a negative control. An anti-human Fc IgG capture chip was used to capture the antibodies, then antigens with different concentrations were used as a mobile phase for the determination, and finally curve fitting was performed according to a 1:1 mode to obtain affinity values. The results are shown in Table 7.

The results showed that 11165, 29C1 (HIL1), and 77H11 (H3L1) had affinities of $10^{-10}$ M to $10^{-11}$ M for both human and monkey MASP2 proteins, and 11165 also had an affinity at the $10^{-10}$ M level for murine MASP2.

TABLE 7

Assay results for affinity ($K_D$) of the anti-MASP2 antibodies

| Antigen | Antibody | ka (1/Ms) | kd (1/s) | $K_D$ (M) |
|---|---|---|---|---|
| Human MASP2 | 11165 | 3.91E+05 | 2.98E−05 | 7.61E−11 |
| | 29C1(H1L1) | 4.10E+05 | 2.94E−05 | 7.16E−11 |
| | 77H11(H3L1) | 7.58E+05 | 6.32E−05 | 8.34E−11 |
| | OMS721 | 9.07E+05 | 3.69E−05 | 4.07E−11 |
| Monkey MASP2 | 11165 | 3.92E+05 | 3.79E−05 | 9.67E−11 |
| | 29C1(H1L1) | 3.54E+05 | 6.83E−05 | 1.93E−10 |
| | 77H11(H3L1) | 6.16E+05 | 8.63E−05 | 1.40E−10 |
| | OMS721 | 9.59E+05 | 2.57E−05 | 2.68E−11 |
| Murine MASP2 | 11165 | 4.41E+06 | 1.92E−03 | 4.35E−10 |
| | 29C1(H1L1) | | No binding | |
| | 77H11(H3L1) | | No binding | |
| | OMS721 | 1.03E+06 | 2.41E−04 | 2.33E−10 |

Example 6. Assay on Inhibition of Lectin Pathway Activity of Different Species by the Anti-MASP2 Antibodies In Vitro The anti-MASP2 antibodies were each assayed for the inhibition of the lectin pathway activity in 90% human, monkey and murine sera.

The identification of the functional activity of the antibodies in 90% human, monkey and murine sera was performed as follows: A 384-well plate was coated with a sodium carbonate-sodium bicarbonate buffer (pH>9) containing 5 μg/mL mannan solution at 25 μL/well and incubated at 4° ° C. overnight. The plate was washed 3 times with TBST with 5 mM $Ca^{2+}$ at 50 μL/well. The plate was blocked with a 3% BSA blocking solution (solvent: TBS, 5 mM $Ca^{2+}$ was added) at 50 μL/well at room temperature for 1.5-2 h. The plate was washed 3 times with TBST at 50 μL/well, once with TBS at 50 μL/well, and once with VBS at 50 μL/well. The MASP2 antibody was diluted with VBS and mixed with human serum at a ratio of 1:9 (i.e., 90% human serum) to obtain a mixture. The mixture was incubated at 4° C. for 30 min and added to the above 384-well plate at 15 μL/well. The mixture was incubated at 4° C. for 1 h. The plate was washed 3 times with TBST at 50 μL/well. A primary antibody diluted with TBS with 0.5% BSA (Biotin-Chicken Anti-C4C, 6 μg/mL) was added at 15 μL/well. The mixture was incubated at room temperature for 60 min. The plate was washed 3 times with TBST at 50 μL/well. A secondary antibody (SA-HRP) diluted in a 1:5000 ratio with a 0.5% BSA solution was added at 15 μL/well. The mixture was incubated at room temperature for 30 min. The plate was washed 3 times again with TBST at 50 μL/well. A TMB chromogenic solution was added at 45 μL/well. The mixture was incubated at room temperature for 15 min in the dark. Finally, a stop solution was added at 45 μL/well, and OD450 values were determined.

Figure 3A:
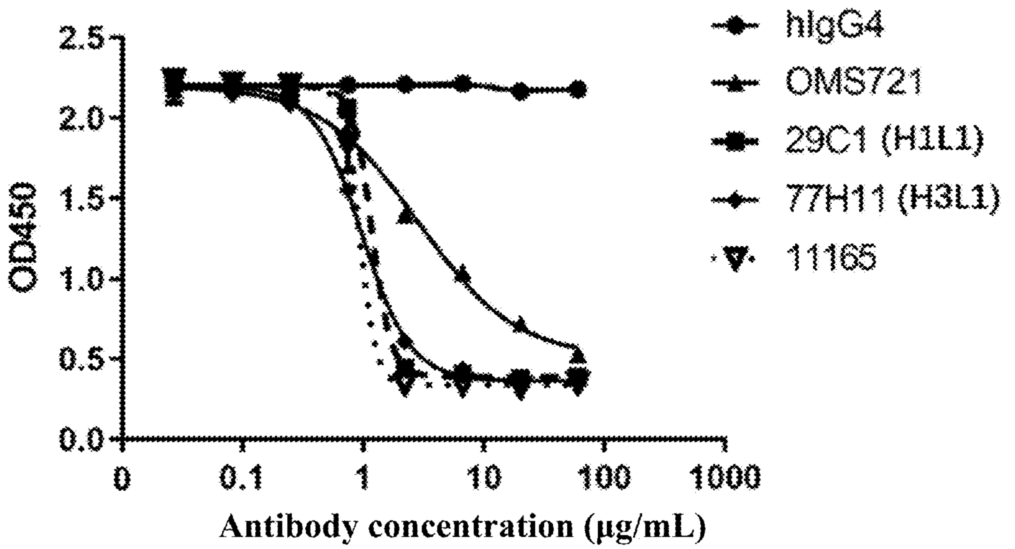
FIGS. 3A-3C are graphs showing assay results for the inhibitory effect of 29C1 (H1L1), 77H11 (H3L1), and 11165 on the lectin pathway in a 90% human serum, a 90% monkey serum, and a 90% mouse serum, respectively, with an isotype control of hIgG4 used as a negative control and OMS721 used as a positive control.
Figure 3B:
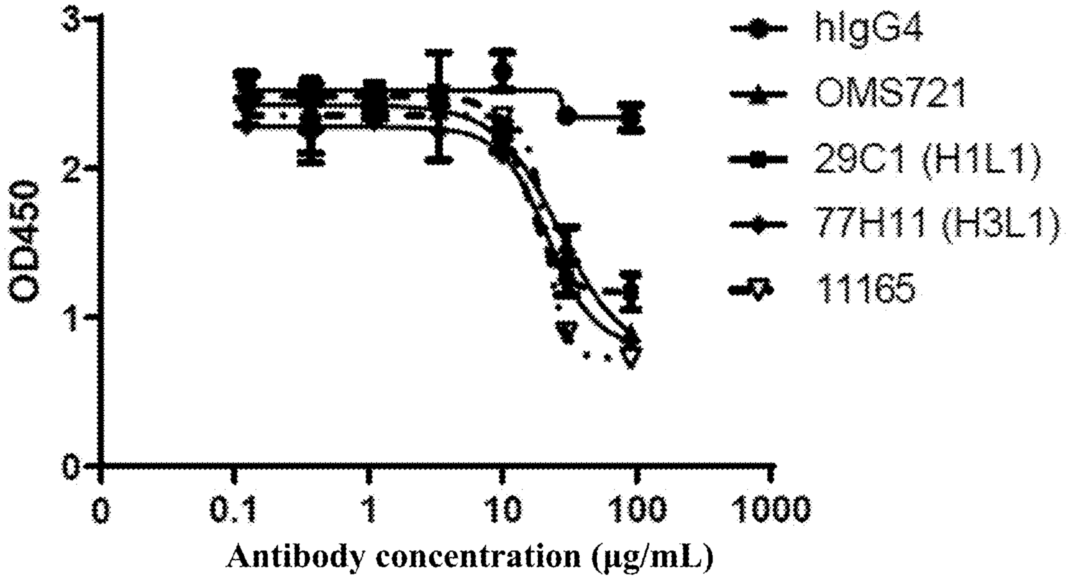
Figure 3C:
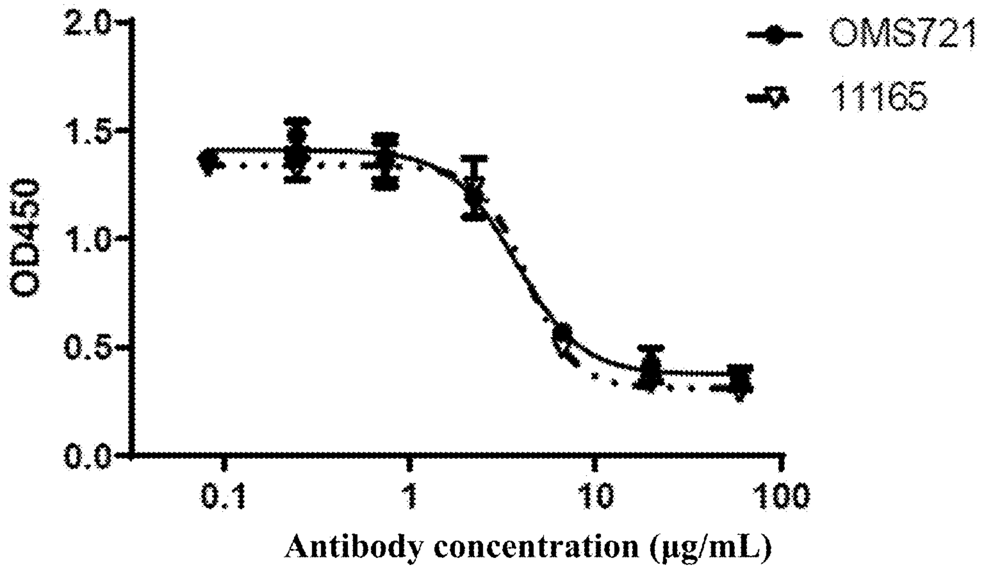

The results are shown in FIGS. 3A-3C and Table 8. The results showed that 11165, 29C1 (HIL1), and 77H11 (H3L1) had superior inhibitory activity for the lectin pathway in human serum to OMS721, with an isotype IgG antibody used as a negative control.

TABLE 8

Inhibitory effect of the anti-MASP2 antibodies on the lectin pathway in sera of different species

| Antibody | 90% human serum $IC_{50}$ (μg/mL) | 90% monkey serum $IC_{50}$ (μg/mL) | 90% mouse serum $IC_{50}$ (μg/mL) |
|---|---|---|---|
| OMS721 | 2.835 | 26.64 | 3.742 |
| 29C1 (H1L1) | 1.178 | 15.28 | / |
| 77H1 (H3L1) | 0.970 | 21.63 | / |
| 11165 | 0.930 | 21.05 | 4.263 |

Example 7. Functional Validation of Anti-MASP2 Antibodies in Animal Models of Cerebral Stroke A general cerebral stroke modeling method was adopted. The method was performed as follows: male C57 mice (body weight: 12-20 g) were injected once intraperitoneally with the drug on day 7 and day 3 before modeling, and injected once with 10 mg/kg drug in the tail vein after 1 h of ischemia (reperfusion at the same time) on the day of modeling. The anesthetized mice were fixed in the supine position on a fixation table, and the skin of the neck was removed before the neck was sterilized with iodophor. A median incision was made in the neck to separate the right common carotid artery (CCA), external carotid artery (ECA), and internal carotid artery (ICA). The proximal end of the CCA and the ICA were temporarily clamped with vascular clamps. A 6-0 surgical thread was provided on the ECA, and the ECA is then burned off with an electrocoagulation pen. A small incision was made in the ECA, and a silicone-coated monofilament was inserted into the incision and gently ligated with a surgical thread. The vascular clamp on the ICA was removed, the silicone-coated monofilament was slowly inserted into the CCA, and into the ICA through the CCA until a slight resistance was encountered, and then the surgical thread on the ECA was tightened to secure the monofilament firmly. The vascular clamp on the CCA was then removed. After 1 h of ischemia, the monofilament was pulled out and the skin of the neck was sutured. The animals were put back in cages for housing. At 48 h of reperfusion, animals were sacrificed and TTC staining was performed for the measurement of cerebral infarct size.

Figure 4:
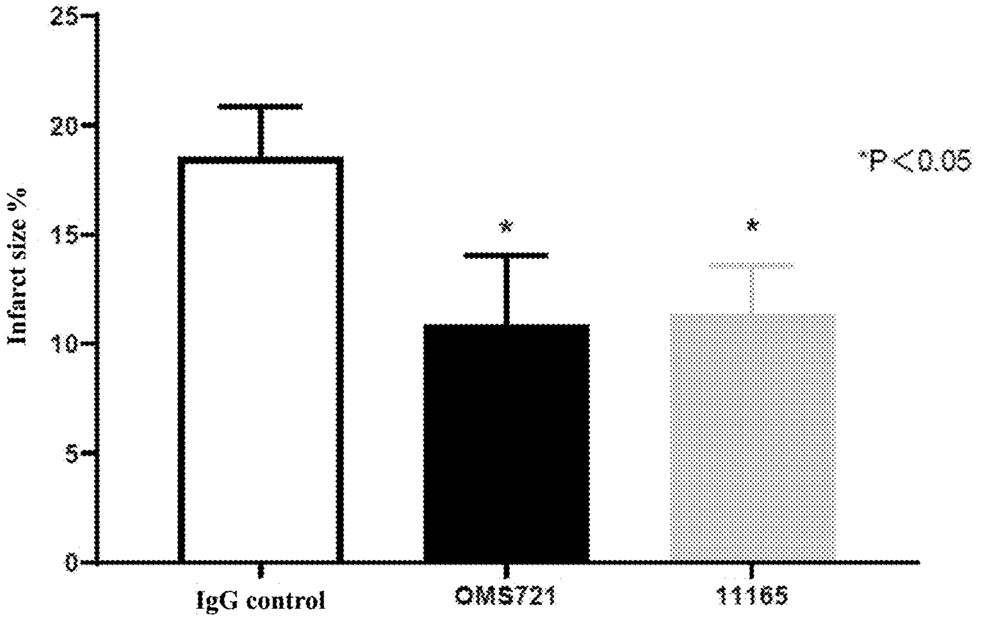
FIG. 4 is a graph showing the proportion of cerebral infarct size, which shows assay results for the protective effect of 11165 and OMS721 in a mouse model of cerebral stroke.

As shown in FIG. 4, the results showed that 11165 and OMS721 were both able to significantly inhibit cerebral infarct size of mice, with an isotype IgG used as a negative control.

Example 8. Experiment on Pharmacodynamics (PD) of Anti-MASP2 Antibodies in Monkeys 77H11 (H3L1), 29C1 (HIL1), 11165, and OMS721 were each administered to cynomolgus monkeys by intravenous bolus injection at doses of 3 mg/kg and 10 mg/kg, and blood was collected at different time points for serum collection. The lectin pathway activity of sera of cynomolgus monkeys collected at different time points was assayed. The specific time points for blood collection were 0 h, 15 min, 1 h, 4 h, 8 h, 24 h, 48 h, 72 h, 96 h, 168 h, 240 h, 360 h, 480 h, 600 h, and 720 h. The method for serum isolation was performed as follows: blood samples were collected from peripheral veins and directly injected into blank blood collection tubes. The blood samples were left to stand for 15-60 min until the blood coagulated, and then centrifuged at 4° C. and 2500 g for 10 min. The supernatant collected was the serum.

Figure 5A:
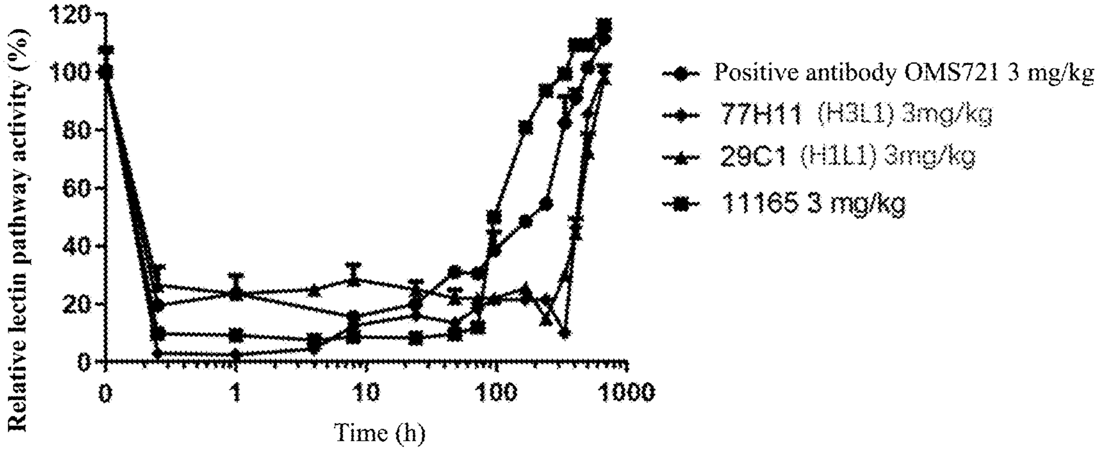
FIGS. 5A-5B are graphs showing assay results for the inhibition of the lectin pathway by 29C1 (H1L1), 77H11 (H3L1), 11165, and OMS721 at doses of 3 mg/kg and 10 mg/kg in cynomolgus monkeys.
Figure 5B:
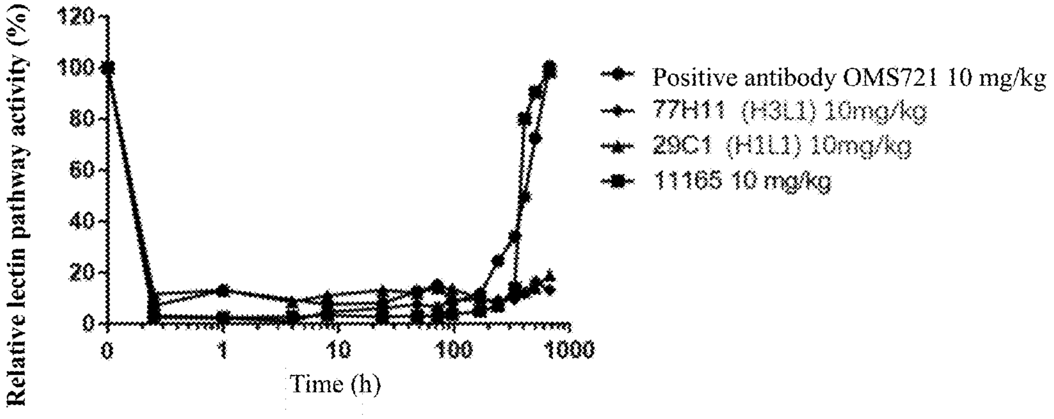

The results are shown in FIGS. 5A and 5B, and it can be seen that the 4 antibodies were all able to significantly inhibit the lectin pathway activity, among which 77H11 (H3L1) and 29C1 (HIL1) had a longer-lasting inhibitory effect than OMS721 at the same dose.

Example 9. Experiment on Pharmacokinetics (PK) of Anti-MASP2 Antibodies in Monkeys Six healthy male cynomolgus monkeys weighing 2-5 kg, which had not previously received macromolecular drugs, were selected. On the day of the experiment, test drugs 77H11 (H3L1), 29C1 (HIL1), 11165, and OMS721 were each administered by intravenous bolus injection at a dose of 3 mg/kg or 10 mg/kg. The blood collection time points after the administration were 15 min, 1 h, 4 h, 8 h, 24 h, 48 h, 72 h, 96 h, 168 h, 240 h, 336 h, 408 h, 504 h, and 672 h. 0.3 mL of whole blood was taken each time without the addition of anticoagulant. After that, the blood was left to stand at 4° C. for 30 min and centrifuged at 1000 g for 15 min. The supernatant was collected and placed in an EP tube, which was then stored at 80° C.

The plasma concentration in the serum was determined by an ELISA method, and $T_{1/2}$ and main parameters thereof of the test drugs were calculated by a matrix fitting method. The results are shown in Table 9. It can be seen that 11165 had a half-life similar to that of OMS721, while 77H11 (H3L1) and 29C1 (HIL1) had half-lives significantly better than that of OMS721, indicating that they had longer-lasting efficacy in vivo.

TABLE 9

Results for PK parameters of the anti-MASP2 antibodies in monkeys

| Antibody (dose of administration) | $T_{1/2}$ (h) | AUC(0-t) (ug/L*h) | AUC(0-∞) (ug/L*h) | $C_{max}$ (ug/L) |
|---|---|---|---|---|
| OMS721 3 mg/kg | 117.70 | 23734.39 | 24303.16 | 163.27 |
| OMS721 10 mg/kg | 157.02 | 38096.56 | 40064.39 | 376.19 |
| 29C1(H1L1) 3 mg/kg | 217.02 | 1055.46 | 23870.92 | 130.63 |
| 29C1(H1L1)10 mg/kg | 278.77 | 56969.76 | 70310.66 | 235.07 |
| 77H11(H3L1) 3 mg/kg | 275.89 | 22222.04 | 27069.52 | 103.87 |
| 77H11(H3L1)10 mg/kg | 583.02 | 52795.70 | 97227.77 | 165.34 |
| 11165 3 mg/kg | 83.57 | 15198.24 | 16032.22 | 136.48 |
| 11165 10 mg/kg | 175.53 | 118419.50 | 128152.55 | 742.03 |

The use and welfare of the laboratory animals in the present disclosure were carried out in compliance with the provisions of Association for Assessment and Accreditation of Laboratory Animal Care, International (AAALAC). The health and death of the animals were monitored daily, and routine examinations included observation of the effects of the test substance and drug on the daily performance of the animals, such as behavioral activities, weight changes and appearance.

Although specific embodiments of the present disclosure have been described above, it will be appreciated by those skilled in the art that these embodiments are merely illustrative and that many changes or modifications can be made to these embodiments without departing from the principles and spirit of the present disclosure.

The invention claimed is:

1. An anti-MASP2 antibody or an antigen-binding fragment thereof, comprising a heavy chain variable region (VH) and a light chain variable region (VL), wherein:

1) The VH comprises a HCDR1, a HCDR2, and a HCDR3 set forth in SEQ ID NOs: 17, 18, and 26, respectively, and the VL comprises a LCDR1, a LCDR2, and a LCDR3 set forth in SEQ ID NOs: 20, 27, and 22, respectively;

2) The VH comprises a HCDR1, a HCDR2, and a HCDR3 set forth in SEQ ID NOs: 28, 29, and 30, respectively, and the VL comprises a LCDR1, a LCDR2, and a LCDR3 set forth in SEQ ID NOs: 31, 32, and 33, respectively; or 3) The VH comprises a HCDR1, a HCDR2, and a HCDR3 set forth in SEQ ID NOs: 34, 35, and 36, respectively, and the VL comprises a LCDR1, a LCDR2, and a LCDR3 set forth in SEQ ID NOs: 37, 38, and 39, respectively.

2. An anti-MASP2 antibody or an antigen-binding fragment thereof, comprising a heavy chain variable region (VH) and a light chain variable region (VL), wherein:

the VH comprises a HCDR1, a HCDR2, and a HCDR3 in a VH set forth in SEQ ID NO: 7, and the VL comprises a LCDR1, a LCDR2, and a LCDR3 in a VL set forth in SEQ ID NO: 8;

the VH comprises a HCDR1, a HCDR2, and a HCDR3 in a VH set forth in SEQ ID NO: 9, and the VL comprises a LCDR1, a LCDR2, and a LCDR3 in a VL set forth in SEQ ID NO: 10;

the VH comprises a HCDR1, a HCDR2, and a HCDR3 in a VH set forth in SEQ ID NO: 11, and the VL comprises a LCDR1, a LCDR2, and a LCDR3 in a VL set forth in SEQ ID NO: 12;

the VH comprises a HCDR1, a HCDR2, and a HCDR3 in a VH set forth in SEQ ID NO: 13, and the VL comprises a LCDR1, a LCDR2, and a LCDR3 in a VL set forth in SEQ ID NO: 14; or the VH comprises a HCDR1, HCDR2, and a HCDR3 in a VH set forth in SEQ ID NO: 15, and the VL comprises a LCDR1, a LCDR2, and a LCDR3 in a VL set forth in SEQ ID NO: 16;

wherein the HCDRs 1-3 and the LCDRs 1-3 are defined according to the Kabat, IMGT, Chothia, AbM, or Contact numbering scheme.

3. The anti-MASP2 antibody or the antigen-binding fragment thereof according to claim 1, wherein the antibody or antigen-binding fragment is a murine antibody, a chimeric antibody, a humanized antibody or a fully human antibody or a fragment thereof.

4. The anti-MASP2 antibody or the antigen-binding fragment thereof according to claim 3, wherein:

the humanized antibody or the antigen-binding fragment thereof comprises a heavy chain framework region derived from IGKV3-21*01 or IGKV4-30-4*01 and/or a light chain framework region derived from IGKV1-33*01 or IGKV1-27*01.

5. The anti-MASP2 antibody or the antigen-binding fragment thereof according to claim 1, wherein:

the VH comprises an amino acid sequence set forth in any one of SEQ ID NOs: 47-50 or an amino acid sequence having at least 90% or at least 95% identity thereto, and the VL comprises an amino acid sequence set forth in SEQ ID NO: 51 or 52 or an amino acid sequence having at least 90% or at least 95% identity thereto;

the VH comprises an amino acid sequence set forth in SEQ ID NO: 7 or an amino acid sequence having at least 90% or at least 95% identity thereto, and the VL comprises an amino acid sequence set forth in SEQ ID NO: 8 or an amino acid sequence having at least 90% or at least 95% identity thereto;

the VH comprises an amino acid sequence set forth in SEQ ID NO: 9 or an amino acid sequence having at least 90% or at least 95% identity thereto, and the VL comprises an amino acid sequence set forth in SEQ ID NO: 10 or an amino acid sequence having at least 90% or at least 95% identity thereto;

the VH comprises an amino acid sequence set forth in SEQ ID NO: 11 or an amino acid sequence having at least 90% or at least 95% identity thereto, and the VL comprises an amino acid sequence set forth in SEQ ID NO: 12 or an amino acid sequence having at least 90% or at least 95% identity thereto;

the VH comprises an amino acid sequence set forth in any one of SEQ ID NOs: 42-44 or an amino acid sequence having at least 90% or at least 95% identity thereto, and the VL comprises an amino acid sequence set forth in SEQ ID NO: 45 or 46 or an amino acid sequence having at least 90% or at least 95% identity thereto;

the VH comprises an amino acid sequence set forth in SEQ ID NO: 13 or an amino acid sequence having at least 90% or at least 95% identity thereto, and the VL comprises an amino acid sequence set forth in SEQ ID NO: 14 or an amino acid sequence having at least 90% or at least 95% identity thereto; or the VH comprises an amino acid sequence set forth in SEQ ID NO: 15 or an amino acid sequence having at least 90% or at least 95% identity thereto, and the VL comprises an amino acid sequence set forth in SEQ ID NO: 16 or an amino acid sequence having at least 90% or at least 95% identity thereto.

6. The anti-MASP2 antibody or the antigen-binding fragment thereof according to claim 1, wherein the anti-MASP2 antibody or the antigen-binding fragment thereof is an IgG1, IgG2, or IgG4 antibody or an antigen-binding fragment thereof.

7. The anti-MASP2 antibody or the antigen-binding fragment thereof according to claim 1, wherein the antigen-binding fragment is an scFv, Fv, Fab, or Fab' fragment.

8. The anti-MASP2 antibody or the antigen-binding fragment thereof according to claim 1, comprising:

1) A heavy chain comprising an amino acid sequence set forth in SEQ ID NO: 56 or an amino acid sequence having at least 90% or at least 95% identity thereto, and a light chain comprising an amino acid sequence set forth in SEQ ID NO: 57 or an amino acid sequence having at least 90% or at least 95% identity thereto;

2) A heavy chain comprising an amino acid sequence set forth in SEQ ID NO: 54 or an amino acid sequence having at least 90% or at least 95% identity thereto, and a light chain comprising an amino acid sequence set forth in SEQ ID NO: 55 or an amino acid sequence having at least 90% or at least 95% identity thereto; or 3) A heavy chain comprising an amino acid sequence set forth in SEQ ID NO: 58 or an amino acid sequence having at least 90% or at least 95% identity thereto, and a light chain comprising an amino acid sequence set forth in SEQ ID NO: 59 or an amino acid sequence having at least 90% or at least 95% identity thereto.

9. The anti-MASP2 antibody or the antigen-binding fragment thereof according to claim 1, having at least one of the following:

(i) the antibody or the antigen-binding fragment binding to human MASP-2 with $K_D$ of 10 nM or less;

(ii) the antibody or the antigen-binding fragment binding to an epitope in a CCP1 domain of MASP-2;

(iii) the antibody or the antigen-binding fragment inhibiting C3b deposition in 1% human serum in an in vitro assay with $IC_{50}$ of 10 nM or less;

(iv) the antibody or the antigen-binding fragment inhibiting C3b deposition in 90% human serum with $IC_{50}$ of 30 nM or less; and (v) the antibody or the antigen-binding fragment substantially having no inhibition of the classic pathway.

10. An isolated polynucleotide encoding the anti-MASP2 antibody or the antigen-binding fragment thereof according to claim 1.

11. An expression vector comprising the polynucleotide according to claim 10.

12. A host cell comprising the expression vector according to claim 11.

13. A method for preparing an anti-MASP2 antibody or antigen-binding fragment thereof, comprising:

culturing the host cell according to claim 12, and isolating the expressed anti-MASP2 antibody or the antigen-binding fragment thereof from the host cell.

14. A pharmaceutical composition comprising the anti-MASP2 antibody or the antigen-binding fragment thereof according to claim 1, and one or more pharmaceutically acceptable excipients, diluents, or carriers.

15. A method for treating a disease, comprising:

administering to a subject in need thereof a therapeutically effective amount of the anti-MASP2 antibody or the antigen-binding fragment thereof according to claim 1, wherein, the disease is related to MASP-2-dependent complement activation.

16. The method according to claim 15, wherein the disease is selected from the group consisting of: IgA nephropathy, paroxysmal nocturnal hemoglobinuria (PNH), lupus nephritis, thrombotic microangiopathy (TMA), hemolytic uremic syndrome (HUS), membranous glomerulonephritis, glomerulonephritis, age-related macular degeneration, reperfusion injury, myocardial infarction, diabetic neuropathy, stroke, graft-versus-host disease (GVHD), and Upshaw-Schulman syndrome (USS).

17. The anti-MASP2 antibody or the antigen-binding fragment thereof according to claim 1, wherein:

the VH comprises a HCDR1, a HCDR2, and a HCDR3 set forth in SEQ ID NOs: 17, 18, and 19, respectively, and the VL comprises a LCDR1, a LCDR2, and a LCDR3 set forth in SEQ ID NOs: 20, 21, and 22, respectively;

the VH comprises a HCDR1, a HCDR2, and a HCDR3 set forth in SEQ ID NOs: 17, 18, and 23, respectively, and the VL comprises a LCDR1, a LCDR2, and a LCDR3 set forth in SEQ ID NOs: 20, 24, and 22, respectively; or the VH comprises a HCDR1, a HCDR2, and a HCDR3 set forth in SEQ ID NOs: 17, 18, and 25, respectively, and the VL comprises a LCDR1, a LCDR2, and a LCDR3 set forth in SEQ ID NOs: 20, 21, and 22, respectively.

* * * * *

SEQUENCE LISTING

<160> NUMBER OF SEQ ID NOS: 61

<210> SEQ ID NO 1
<211> LENGTH: 707
<212> TYPE: PRT
<213> ORGANISM: Artificial sequence
<220> FEATURE:
<223> OTHER INFORMATION: Human MASP2A protein

<400> SEQUENCE: 1

Met Glu Phe Gly Leu Ser Trp Leu Phe Leu Val Ala Ile Leu Lys Gly
1 5 10 15

Val Gln Cys Thr Pro Leu Gly Pro Lys Trp Pro Glu Pro Val Phe Gly
20 25 30

Arg Leu Ala Ser Pro Gly Phe Pro Gly Glu Tyr Ala Asn Asp Gln Glu
35 40 45

Arg Arg Trp Thr Leu Thr Ala Pro Pro Gly Tyr Arg Leu Arg Leu Tyr
50 55 60

Phe Thr His Phe Asp Leu Glu Leu Ser His Leu Cys Glu Tyr Asp Phe
65 70 75 80

Val Lys Leu Ser Ser Gly Ala Lys Val Leu Ala Thr Leu Cys Gly Gln
85 90 95

Glu Ser Thr Asp Thr Glu Arg Ala Pro Gly Lys Asp Thr Phe Tyr Ser
100 105 110

Leu Gly Ser Ser Leu Asp Ile Thr Phe Arg Ser Asp Tyr Ser Asn Glu
115 120 125

Lys Pro Phe Thr Gly Phe Glu Ala Phe Tyr Ala Ala Glu Asp Ile Asp
130 135 140

Glu Cys Gln Val Ala Pro Gly Glu Ala Pro Thr Cys Asp His His Cys
145 150 155 160

His Asn His Leu Gly Gly Phe Tyr Cys Ser Cys Arg Ala Gly Tyr Val
165 170 175

Leu His Arg Asn Lys Arg Thr Cys Ser Ala Leu Cys Ser Gly Gln Val
180 185 190

Phe Thr Gln Arg Ser Gly Glu Leu Ser Ser Pro Glu Tyr Pro Arg Pro
195 200 205

Tyr Pro Lys Leu Ser Ser Cys Thr Tyr Ser Ile Ser Leu Glu Glu Gly
210 215 220

```
Phe Ser Val Ile Leu Asp Phe Val Glu Ser Phe Asp Val Glu Thr His
225                 230                 235                 240

Pro Glu Thr Leu Cys Pro Tyr Asp Phe Leu Lys Ile Gln Thr Asp Arg
                245                 250                 255

Glu Glu His Gly Pro Phe Cys Gly Lys Thr Leu Pro His Arg Ile Glu
            260                 265                 270

Thr Lys Ser Asn Thr Val Thr Ile Thr Phe Val Thr Asp Glu Ser Gly
        275                 280                 285

Asp His Thr Gly Trp Lys Ile His Tyr Thr Ser Thr Ala Gln Pro Cys
    290                 295                 300

Pro Tyr Pro Met Ala Pro Pro Asn Gly His Val Ser Pro Val Gln Ala
305                 310                 315                 320

Lys Tyr Ile Leu Lys Asp Ser Phe Ser Ile Phe Cys Glu Thr Gly Tyr
                325                 330                 335

Glu Leu Leu Gln Gly His Leu Pro Leu Lys Ser Phe Thr Ala Val Cys
            340                 345                 350

Gln Lys Asp Gly Ser Trp Asp Arg Pro Met Pro Ala Cys Ser Ile Val
        355                 360                 365

Asp Cys Gly Pro Pro Asp Asp Leu Pro Ser Gly Arg Val Glu Tyr Ile
    370                 375                 380

Thr Gly Pro Gly Val Thr Thr Tyr Lys Ala Val Ile Gln Tyr Ser Cys
385                 390                 395                 400

Glu Glu Thr Phe Tyr Thr Met Lys Val Asn Asp Gly Lys Tyr Val Cys
                405                 410                 415

Glu Ala Asp Gly Phe Trp Thr Ser Ser Lys Gly Glu Lys Ser Leu Pro
            420                 425                 430

Val Cys Glu Pro Val Cys Gly Leu Ser Ala Arg Thr Thr Gly Gly Arg
        435                 440                 445

Ile Tyr Gly Gly Gln Lys Ala Lys Pro Gly Asp Phe Pro Trp Gln Val
    450                 455                 460

Leu Ile Leu Gly Gly Thr Thr Ala Ala Gly Ala Leu Leu Tyr Asp Asn
465                 470                 475                 480

Trp Val Leu Thr Ala Ala His Ala Val Tyr Glu Gln Lys His Asp Ala
                485                 490                 495

Ser Ala Leu Asp Ile Arg Met Gly Thr Leu Lys Arg Leu Ser Pro His
            500                 505                 510

Tyr Thr Gln Ala Trp Ser Glu Ala Val Phe Ile His Glu Gly Tyr Thr
        515                 520                 525

His Asp Ala Gly Phe Asp Asn Asp Ile Ala Leu Ile Lys Leu Asn Asn
    530                 535                 540

Lys Val Val Ile Asn Ser Asn Ile Thr Pro Ile Cys Leu Pro Arg Lys
545                 550                 555                 560

Glu Ala Glu Ser Phe Met Arg Thr Asp Asp Ile Gly Thr Ala Ser Gly
                565                 570                 575

Trp Gly Leu Thr Gln Arg Gly Phe Leu Ala Arg Asn Leu Met Tyr Val
            580                 585                 590

Asp Ile Pro Ile Val Asp His Gln Lys Cys Thr Ala Ala Tyr Glu Lys
        595                 600                 605

Pro Pro Tyr Pro Arg Gly Ser Val Thr Ala Asn Met Leu Cys Ala Gly
    610                 615                 620

Leu Glu Ser Gly Gly Lys Asp Ser Cys Arg Gly Asp Ala Gly Gly Ala
625                 630                 635                 640
```

Leu Val Phe Leu Asp Ser Glu Thr Glu Arg Trp Phe Val Gly Gly Ile
645 650 655

Val Ser Trp Gly Ser Met Asn Cys Gly Glu Ala Gly Gln Tyr Gly Val
660 665 670

Tyr Thr Lys Val Ile Asn Tyr Ile Pro Trp Ile Glu Asn Ile Ile Ser
675 680 685

Asp Phe Gly Gly Ser Asp Tyr Lys Asp Asp Asp Asp Lys His His His
690 695 700

His His His
705

<210> SEQ ID NO 2
<211> LENGTH: 707
<212> TYPE: PRT
<213> ORGANISM: Artificial sequence
<220> FEATURE:
<223> OTHER INFORMATION: Monkey MASP2A protein

<400> SEQUENCE: 2

Met Glu Phe Gly Leu Ser Trp Leu Phe Leu Val Ala Ile Leu Lys Gly
1 5 10 15

Val Gln Cys Thr Pro Leu Gly Pro Lys Trp Pro Glu Pro Val Phe Gly
20 25 30

Arg Leu Ala Ser Pro Gly Phe Pro Gly Glu Tyr Ala Asn Asp Gln Glu
35 40 45

Arg Arg Trp Thr Leu Thr Ala Pro Pro Gly Tyr Arg Leu Arg Leu Tyr
50 55 60

Phe Thr His Phe Asp Leu Glu Leu Ser His Leu Cys Glu Tyr Asp Phe
65 70 75 80

Val Lys Leu Ser Ser Gly Ala Lys Val Leu Ala Thr Leu Cys Gly His
85 90 95

Glu Ser Thr Asp Thr Glu Arg Ala Pro Gly Asn Asp Thr Phe Tyr Ser
100 105 110

Leu Gly Ser Ser Leu Asp Ile Thr Phe Arg Ser Asp Tyr Ser Asn Glu
115 120 125

Lys Pro Phe Thr Gly Phe Glu Ala Phe Tyr Ala Ala Glu Asp Ile Asp
130 135 140

Glu Cys Gln Val Ala Pro Gly Glu Ala Pro Ala Cys Asp His His Cys
145 150 155 160

His Asn His Leu Gly Gly Phe Tyr Cys Ser Cys Arg Val Gly Tyr Ile
165 170 175

Leu His Arg Asn Lys Arg Thr Cys Ser Ala Leu Cys Ser Gly Gln Val
180 185 190

Phe Thr Gln Arg Ser Gly Glu Leu Ser Ser Pro Glu Tyr Pro Gln Pro
195 200 205

Tyr Pro Lys Leu Ser Ser Cys Thr Tyr Ser Ile Arg Leu Glu Glu Gly
210 215 220

Phe Ser Val Ile Leu Asp Phe Val Glu Ser Phe Asp Val Glu Thr His
225 230 235 240

Pro Glu Thr Leu Cys Pro Tyr Asp Phe Leu Lys Ile Gln Ile Asp Ser
245 250 255

Glu Glu His Gly Pro Phe Cys Gly Lys Thr Leu Pro Arg Arg Ile Glu
260 265 270

Thr Lys Ser Asn Thr Val Thr Ile Thr Phe Val Thr Asp Glu Ser Gly
275 280 285

```
Asp His Thr Gly Trp Lys Ile His Tyr Thr Ser Thr Ala Gln Pro Cys
    290                 295                 300

Pro Tyr Pro Met Ala Pro Pro Asn Gly His Leu Ser Pro Val Gln Ala
305                 310                 315                 320

Lys Tyr Ile Leu Lys Asp Ser Phe Ser Ile Phe Cys Glu Pro Gly Tyr
                325                 330                 335

Glu Leu Leu Gln Gly His Leu Pro Leu Lys Ser Phe Ala Ala Val Cys
            340                 345                 350

Gln Lys Asp Gly Ser Trp Asp Gln Pro Met Pro Ser Cys Ser Ile Val
        355                 360                 365

Asp Cys Gly Pro Pro Asp Asp Leu Pro Ser Gly Arg Val Glu Tyr Ile
    370                 375                 380

Thr Gly Pro Glu Val Thr Thr Tyr Lys Ala Val Ile Gln Tyr Ser Cys
385                 390                 395                 400

Glu Glu Thr Phe Tyr Thr Met Lys Val Asn Asp Gly Lys Tyr Val Cys
                405                 410                 415

Glu Ala Asp Gly Phe Trp Thr Ser Ser Lys Gly Glu Arg Ser Pro Pro
            420                 425                 430

Val Cys Glu Pro Val Cys Gly Leu Ser Ala Arg Thr Thr Gly Gly Arg
        435                 440                 445

Ile Tyr Gly Gly Gln Lys Ala Lys Pro Gly Asp Phe Pro Trp Gln Val
    450                 455                 460

Leu Ile Leu Gly Gly Ser Thr Ala Ala Gly Ala Leu Leu Tyr Asp Asn
465                 470                 475                 480

Trp Val Leu Thr Ala Ala His Ala Ile Tyr Glu Gln Lys His Asp Ala
                485                 490                 495

Ser Ser Leu Asp Ile Arg Leu Gly Ala Leu Lys Arg Leu Ser Pro His
            500                 505                 510

Tyr Thr Gln Ala Trp Ala Glu Ala Val Phe Ile His Glu Gly Tyr Thr
        515                 520                 525

His Asp Ala Gly Phe Asp Asn Asp Ile Ala Leu Ile Lys Leu Asn Asn
    530                 535                 540

Lys Val Val Ile Asn Ser Asn Ile Thr Pro Ile Cys Leu Pro Arg Lys
545                 550                 555                 560

Glu Ala Glu Ser Phe Met Arg Thr Asp Asp Ile Gly Thr Ala Ser Gly
                565                 570                 575

Trp Gly Leu Thr Gln Arg Gly Leu Leu Ala Arg Asn Leu Met Tyr Val
            580                 585                 590

Asp Ile Pro Ile Val Asp His Gln Lys Cys Thr Ala Ala Tyr Glu Lys
        595                 600                 605

Pro Pro Tyr Ser Gly Gly Ser Val Thr Ala Asn Met Leu Cys Ala Gly
    610                 615                 620

Leu Glu Ser Gly Gly Lys Asp Ser Cys Arg Gly Asp Ala Gly Gly Ala
625                 630                 635                 640

Leu Val Phe Leu Asp Asn Glu Thr Gln Arg Trp Phe Val Gly Gly Ile
                645                 650                 655

Val Ser Trp Gly Ser Met Asn Cys Gly Glu Ala Gly Gln Tyr Gly Val
            660                 665                 670

Tyr Thr Lys Val Ile Asn Tyr Ile Pro Trp Ile Lys Asn Ile Ile Ser
        675                 680                 685

Asn Phe Gly Gly Ser Asp Tyr Lys Asp Asp Asp Asp Lys His His His
    690                 695                 700

His His His
```

705

<210> SEQ ID NO 3
<211> LENGTH: 706
<212> TYPE: PRT
<213> ORGANISM: Artificial sequence
<220> FEATURE:
<223> OTHER INFORMATION: Murine MASP2A protein

<400> SEQUENCE: 3

```
Met Glu Phe Gly Leu Ser Trp Leu Phe Leu Val Ala Ile Leu Lys Gly
1               5                   10                  15

Val Gln Cys Thr Pro Leu Gly Ser Lys Trp Pro Glu Pro Val Phe Gly
            20                  25                  30

Arg Leu Val Ser Pro Gly Phe Pro Glu Lys Tyr Ala Asp His Gln Asp
        35                  40                  45

Arg Ser Trp Thr Leu Thr Ala Pro Pro Gly Tyr Arg Leu Arg Leu Tyr
    50                  55                  60

Phe Thr His Phe Asp Leu Glu Leu Ser Tyr Arg Cys Glu Tyr Asp Phe
65                  70                  75                  80

Val Lys Leu Ser Ser Gly Thr Lys Val Leu Ala Thr Leu Cys Gly Gln
                85                  90                  95

Glu Ser Thr Asp Thr Glu Gln Ala Pro Gly Asn Asp Thr Phe Tyr Ser
            100                 105                 110

Leu Gly Pro Ser Leu Lys Val Thr Phe His Ser Asp Tyr Ser Asn Glu
        115                 120                 125

Lys Pro Phe Thr Gly Phe Glu Ala Phe Tyr Ala Ala Glu Asp Val Asp
    130                 135                 140

Glu Cys Arg Val Ser Leu Gly Asp Ser Val Pro Cys Asp His Tyr Cys
145                 150                 155                 160

His Asn Tyr Leu Gly Gly Tyr Tyr Cys Ser Cys Arg Ala Gly Tyr Val
                165                 170                 175

Leu His Gln Asn Lys His Thr Cys Ser Ala Leu Cys Ser Gly Gln Val
            180                 185                 190

Phe Thr Gly Arg Ser Gly Tyr Leu Ser Ser Pro Glu Tyr Pro Gln Pro
        195                 200                 205

Tyr Pro Lys Leu Ser Ser Cys Thr Tyr Ser Ile Arg Leu Glu Asp Gly
    210                 215                 220

Phe Ser Val Ile Leu Asp Phe Val Glu Ser Phe Asp Val Glu Thr His
225                 230                 235                 240

Pro Glu Ala Gln Cys Pro Tyr Asp Ser Leu Lys Ile Gln Thr Asp Lys
                245                 250                 255

Gly Glu His Gly Pro Phe Cys Gly Lys Thr Leu Pro Pro Arg Ile Glu
            260                 265                 270

Thr Asp Ser His Lys Val Thr Ile Thr Phe Ala Thr Asp Glu Ser Gly
        275                 280                 285

Asn His Thr Gly Trp Lys Ile His Tyr Thr Ser Thr Ala Arg Pro Cys
    290                 295                 300

Pro Asp Pro Thr Ala Pro Pro Asn Gly Ser Ile Ser Pro Val Gln Ala
305                 310                 315                 320

Ile Tyr Val Leu Lys Asp Arg Phe Ser Val Phe Cys Lys Thr Gly Phe
                325                 330                 335

Glu Leu Leu Gln Gly Ser Val Pro Leu Lys Ser Phe Thr Ala Val Cys
            340                 345                 350

Gln Lys Asp Gly Ser Trp Asp Arg Pro Met Pro Glu Cys Ser Ile Ile
```

```
        355                 360                 365

Asp Cys Gly Pro Pro Asp Asp Leu Pro Asn Gly His Val Asp Tyr Ile
    370                 375                 380

Thr Gly Pro Glu Val Thr Thr Tyr Lys Ala Val Ile Gln Tyr Ser Cys
385                 390                 395                 400

Glu Glu Thr Phe Tyr Thr Met Ser Ser Asn Gly Lys Tyr Val Cys Glu
                405                 410                 415

Ala Asp Gly Phe Trp Thr Ser Ser Lys Gly Glu Lys Leu Pro Pro Val
            420                 425                 430

Cys Glu Pro Val Cys Gly Leu Ser Thr His Thr Ile Gly Gly Arg Ile
        435                 440                 445

Val Gly Gly Gln Pro Ala Lys Pro Gly Asp Phe Pro Trp Gln Val Leu
    450                 455                 460

Leu Leu Gly Gln Thr Thr Ala Ala Ala Gly Ala Leu Ile His Asp Asn
465                 470                 475                 480

Trp Val Leu Thr Ala Ala His Ala Val Tyr Glu Lys Arg Met Ala Ala
                485                 490                 495

Ser Ser Leu Asn Ile Arg Met Gly Ile Leu Lys Arg Leu Ser Pro His
            500                 505                 510

Tyr Thr Gln Ala Trp Pro Glu Glu Ile Phe Ile His Glu Gly Tyr Thr
        515                 520                 525

His Gly Ala Gly Phe Asp Asn Asp Ile Ala Leu Ile Lys Leu Lys Asn
    530                 535                 540

Lys Val Thr Ile Asn Gly Ser Ile Met Pro Val Cys Leu Pro Arg Lys
545                 550                 555                 560

Glu Ala Ala Ser Leu Met Arg Thr Asp Phe Thr Gly Thr Val Ala Gly
                565                 570                 575

Trp Gly Leu Thr Gln Lys Gly Leu Leu Ala Arg Asn Leu Met Phe Val
            580                 585                 590

Asp Ile Pro Ile Ala Asp His Gln Lys Cys Thr Ala Val Tyr Glu Lys
        595                 600                 605

Leu Tyr Pro Gly Val Arg Val Ser Ala Asn Met Leu Cys Ala Gly Leu
    610                 615                 620

Glu Thr Gly Gly Lys Asp Ser Cys Arg Gly Asp Ala Gly Gly Ala Leu
625                 630                 635                 640

Val Phe Leu Asp Asn Glu Thr Gln Arg Trp Phe Val Gly Gly Ile Val
                645                 650                 655

Ser Trp Gly Ser Ile Asn Cys Gly Ala Ala Asp Gln Tyr Gly Val Tyr
            660                 665                 670

Thr Lys Val Ile Asn Tyr Ile Pro Trp Ile Glu Asn Ile Ile Ser Asn
        675                 680                 685

Phe Gly Gly Ser Asp Tyr Lys Asp Asp Asp Asp Lys His His His His
    690                 695                 700

His His
705


<210> SEQ ID NO 4
<211> LENGTH: 421
<212> TYPE: PRT
<213> ORGANISM: Artificial sequence
<220> FEATURE:
<223> OTHER INFORMATION: Human MASP2 CCP1-CCP2-SP

<400> SEQUENCE: 4

Met Gly Ser Ser His His His His His His Ser Ser Gly Leu Val Pro
```

-continued

```
1               5                   10                  15

Arg Gly Ser His Met Thr Gly Trp Lys Ile His Tyr Thr Ser Thr Ala
            20                  25                  30

Gln Pro Cys Pro Tyr Pro Met Ala Pro Pro Asn Gly His Val Ser Pro
        35                  40                  45

Val Gln Ala Lys Tyr Ile Leu Lys Asp Ser Phe Ser Ile Phe Cys Glu
    50                  55                  60

Thr Gly Tyr Glu Leu Leu Gln Gly His Leu Pro Leu Lys Ser Phe Thr
65                  70                  75                  80

Ala Val Cys Gln Lys Asp Gly Ser Trp Asp Arg Pro Met Pro Ala Cys
                85                  90                  95

Ser Ile Val Asp Cys Gly Pro Pro Asp Asp Leu Pro Ser Gly Arg Val
            100                 105                 110

Glu Tyr Ile Thr Gly Pro Gly Val Thr Thr Tyr Lys Ala Val Ile Gln
        115                 120                 125

Tyr Ser Cys Glu Glu Thr Phe Tyr Thr Met Lys Val Asn Asp Gly Lys
    130                 135                 140

Tyr Val Cys Glu Ala Asp Gly Phe Trp Thr Ser Ser Lys Gly Glu Lys
145                 150                 155                 160

Ser Leu Pro Val Cys Glu Pro Val Cys Gly Leu Ser Ala Arg Thr Thr
                165                 170                 175

Gly Gly Arg Ile Tyr Gly Gly Gln Lys Ala Lys Pro Gly Asp Phe Pro
            180                 185                 190

Trp Gln Val Leu Ile Leu Gly Gly Thr Thr Ala Ala Gly Ala Leu Leu
        195                 200                 205

Tyr Asp Asn Trp Val Leu Thr Ala Ala His Ala Val Tyr Glu Gln Lys
    210                 215                 220

His Asp Ala Ser Ala Leu Asp Ile Arg Met Gly Thr Leu Lys Arg Leu
225                 230                 235                 240

Ser Pro His Tyr Thr Gln Ala Trp Ser Glu Ala Val Phe Ile His Glu
                245                 250                 255

Gly Tyr Thr His Asp Ala Gly Phe Asp Asn Asp Ile Ala Leu Ile Lys
            260                 265                 270

Leu Asn Asn Lys Val Val Ile Asn Ser Asn Ile Thr Pro Ile Cys Leu
        275                 280                 285

Pro Arg Lys Glu Ala Glu Ser Phe Met Arg Thr Asp Asp Ile Gly Thr
    290                 295                 300

Ala Ser Gly Trp Gly Leu Thr Gln Arg Gly Phe Leu Ala Arg Asn Leu
305                 310                 315                 320

Met Tyr Val Asp Ile Pro Ile Val Asp His Gln Lys Cys Thr Ala Ala
                325                 330                 335

Tyr Glu Lys Pro Pro Tyr Pro Arg Gly Ser Val Thr Ala Asn Met Leu
            340                 345                 350

Cys Ala Gly Leu Glu Ser Gly Gly Lys Asp Ser Cys Arg Gly Asp Ala
        355                 360                 365

Gly Gly Ala Leu Val Phe Leu Asp Ser Glu Thr Glu Arg Trp Phe Val
    370                 375                 380

Gly Gly Ile Val Ser Trp Gly Ser Met Asn Cys Gly Glu Ala Gly Gln
385                 390                 395                 400

Tyr Gly Val Tyr Thr Lys Val Ile Asn Tyr Ile Pro Trp Ile Glu Asn
                405                 410                 415

Ile Ile Ser Asp Phe
            420
```

<210> SEQ ID NO 5
<211> LENGTH: 345
<212> TYPE: PRT
<213> ORGANISM: Artificial sequence
<220> FEATURE:
<223> OTHER INFORMATION: Human MASP2 CCP2-SP

<400> SEQUENCE: 5

```
Met Gly Ser Ser His His His His His His Ser Ser Gly Leu Val Pro
1               5                   10                  15

Arg Gly Ser His Met Ile Val Asp Cys Gly Pro Pro Asp Asp Leu Pro
            20                  25                  30

Ser Gly Arg Val Glu Tyr Ile Thr Gly Pro Gly Val Thr Thr Tyr Lys
        35                  40                  45

Ala Val Ile Gln Tyr Ser Cys Glu Glu Thr Phe Tyr Thr Met Lys Val
    50                  55                  60

Asn Asp Gly Lys Tyr Val Cys Glu Ala Asp Gly Phe Trp Thr Ser Ser
65                  70                  75                  80

Lys Gly Glu Lys Ser Leu Pro Val Cys Glu Pro Val Cys Gly Leu Ser
                85                  90                  95

Ala Arg Thr Thr Gly Gly Arg Ile Tyr Gly Gly Gln Lys Ala Lys Pro
            100                 105                 110

Gly Asp Phe Pro Trp Gln Val Leu Ile Leu Gly Gly Thr Thr Ala Ala
        115                 120                 125

Gly Ala Leu Leu Tyr Asp Asn Trp Val Leu Thr Ala Ala His Ala Val
    130                 135                 140

Tyr Glu Gln Lys His Asp Ala Ser Ala Leu Asp Ile Arg Met Gly Thr
145                 150                 155                 160

Leu Lys Arg Leu Ser Pro His Tyr Thr Gln Ala Trp Ser Glu Ala Val
                165                 170                 175

Phe Ile His Glu Gly Tyr Thr His Asp Ala Gly Phe Asp Asn Asp Ile
            180                 185                 190

Ala Leu Ile Lys Leu Asn Asn Lys Val Val Ile Asn Ser Asn Ile Thr
        195                 200                 205

Pro Ile Cys Leu Pro Arg Lys Glu Ala Glu Ser Phe Met Arg Thr Asp
    210                 215                 220

Asp Ile Gly Thr Ala Ser Gly Trp Gly Leu Thr Gln Arg Gly Phe Leu
225                 230                 235                 240

Ala Arg Asn Leu Met Tyr Val Asp Ile Pro Ile Val Asp His Gln Lys
                245                 250                 255

Cys Thr Ala Ala Tyr Glu Lys Pro Pro Tyr Pro Arg Gly Ser Val Thr
            260                 265                 270

Ala Asn Met Leu Cys Ala Gly Leu Glu Ser Gly Gly Lys Asp Ser Cys
        275                 280                 285

Arg Gly Asp Ala Gly Gly Ala Leu Val Phe Leu Asp Ser Glu Thr Glu
    290                 295                 300

Arg Trp Phe Val Gly Gly Ile Val Ser Trp Gly Ser Met Asn Cys Gly
305                 310                 315                 320

Glu Ala Gly Gln Tyr Gly Val Tyr Thr Lys Val Ile Asn Tyr Ile Pro
                325                 330                 335

Trp Ile Glu Asn Ile Ile Ser Asp Phe
            340                 345
```

<210> SEQ ID NO 6

<211> LENGTH: 104
<212> TYPE: PRT
<213> ORGANISM: Homo sapiens

<400> SEQUENCE: 6

```
Met Asp Ala Met Lys Arg Gly Leu Cys Cys Val Leu Leu Leu Cys Gly
1               5                   10                  15

Ala Val Phe Val Ser Pro Ser Tyr Thr Ser Thr Ala His Ala Cys Pro
            20                  25                  30

Tyr Pro Met Ala Pro Pro Asn Gly His Val Ser Pro Val Gln Ala Lys
        35                  40                  45

Tyr Ile Leu Lys Asp Ser Phe Ser Ile Phe Cys Glu Thr Gly Tyr Glu
    50                  55                  60

Leu Leu Gln Gly His Leu Pro Leu Lys Ser Phe Thr Ala Val Cys Gln
65                  70                  75                  80

Lys Asp Gly Ser Trp Asp Arg Pro Met Pro Ala Cys Ser Ala His His
                85                  90                  95

His His His His His His His His
            100
```

<210> SEQ ID NO 7
<211> LENGTH: 115
<212> TYPE: PRT
<213> ORGANISM: Murine

<400> SEQUENCE: 7

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Arg Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Val Leu Tyr Ala Leu Asp Tyr Trp Gly Gln Gly Thr Ser Val Thr
            100                 105                 110

Val Ser Ser
        115
```

<210> SEQ ID NO 8
<211> LENGTH: 107
<212> TYPE: PRT
<213> ORGANISM: Murine

<400> SEQUENCE: 8

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60
```

```
Ser Gly Ser Gly Thr Asp Phe Thr Leu Thr Ile Ser Asp Val Gln Ser
65                  70                  75                  80

Glu Asp Leu Ala Glu Tyr Phe Cys Gln Gln Tyr Asn Ser Asn Pro Leu
                85                  90                  95

Thr Phe Gly Ser Gly Thr Lys Leu Glu Ile Lys
            100                 105


<210> SEQ ID NO 9
<211> LENGTH: 115
<212> TYPE: PRT
<213> ORGANISM: Murine

<400> SEQUENCE: 9

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Arg Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ile Leu Tyr Ala Met Asn Phe Trp Gly Gln Gly Thr Ser Val Thr
            100                 105                 110

Val Ser Ser
        115


<210> SEQ ID NO 10
<211> LENGTH: 107
<212> TYPE: PRT
<213> ORGANISM: Murine

<400> SEQUENCE: 10

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Asn Pro Leu
                85                  90                  95

Thr Phe Gly Ser Gly Thr Lys Leu Glu Ile Lys
            100                 105


<210> SEQ ID NO 11
<211> LENGTH: 115
<212> TYPE: PRT
<213> ORGANISM: Murine

<400> SEQUENCE: 11

Asp Val Gln Leu Gln Glu Ser Gly Pro Gly Leu Val Lys Pro Ser Gln
```

```
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Arg Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ile Leu Tyr Ala Met Asp Tyr Trp Gly Gln Gly Thr Ser Val Thr
            100                 105                 110

Val Ser Ser
        115


<210> SEQ ID NO 12
<211> LENGTH: 107
<212> TYPE: PRT
<213> ORGANISM: Murine

<400> SEQUENCE: 12

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Asn Pro Leu
                85                  90                  95

Thr Phe Gly Ser Gly Thr Lys Leu Glu Ile Lys
            100                 105


<210> SEQ ID NO 13
<211> LENGTH: 122
<212> TYPE: PRT
<213> ORGANISM: Murine

<400> SEQUENCE: 13

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Phe
            20                  25                  30

Ala Leu Ser Trp Val Arg Gln Thr Pro Glu Lys Arg Leu Glu Trp Val
        35                  40                  45

Ala Ala Val Ser Arg Gly Gly Asp Tyr Thr Tyr Tyr Pro Asp Ser Met
    50                  55                  60

Lys Gly Arg Phe Thr Ile Ser Arg Asp Asn Ala Met Asn Thr Leu Tyr
65                  70                  75                  80

Leu Gln Met Ser Ser Leu Ser Ser Glu Asp Thr Ala Met Tyr Tyr Cys
                85                  90                  95

Ala Arg His Leu Tyr Gly Tyr Gly His Tyr Tyr Ala Met Asp Tyr Trp
```

```
            100                 105                 110

Gly Gln Gly Thr Ser Val Thr Val Ser Ser
        115                 120


<210> SEQ ID NO 14
<211> LENGTH: 107
<212> TYPE: PRT
<213> ORGANISM: Murine

<400> SEQUENCE: 14

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys
            100                 105


<210> SEQ ID NO 15
<211> LENGTH: 122
<212> TYPE: PRT
<213> ORGANISM: Murine

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Glu Tyr Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Leu Lys Ala Ala Arg Arg Asp Ala Phe Asp Ile Trp
            100                 105                 110

Gly Gln Gly Thr Thr Val Thr Val Ser Ser
        115                 120


<210> SEQ ID NO 16
<211> LENGTH: 106
<212> TYPE: PRT
<213> ORGANISM: Murine

<400> SEQUENCE: 16

Gln Ser Val Leu Thr Gln Pro Pro Ser Val Ser Val Ser Pro Gly Gln
1               5                   10                  15

Thr Ala Ser Ile Thr Cys Ser Gly His Lys Leu Gly Asp Lys Tyr Ala
            20                  25                  30
```

-continued

```
Tyr Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Phe
    50                  55                  60

Asn Ser Gly Asn Thr Ala Thr Leu Thr Ile Ser Gly Thr Gln Ala Thr
65                  70                  75                  80

Asp Glu Ala Asp Tyr Tyr Cys Gln Thr Trp Asp Ser Ser Thr Gly Val
                85                  90                  95

Phe Gly Ala Gly Thr Lys Val Thr Val Leu
            100                 105


<210> SEQ ID NO 17
<211> LENGTH: 6
<212> TYPE: PRT
<213> ORGANISM: Murine

<400> SEQUENCE: 17

Ser Asp Tyr Ala Trp Asn
1               5


<210> SEQ ID NO 18
<211> LENGTH: 16
<212> TYPE: PRT
<213> ORGANISM: Murine

<400> SEQUENCE: 18

Tyr Ile Ser Tyr Ser Gly Arg Thr Ser Tyr Asn Pro Ser Leu Lys Ser
1               5                   10                  15


<210> SEQ ID NO 19
<211> LENGTH: 6
<212> TYPE: PRT
<213> ORGANISM: Murine

<400> SEQUENCE: 19

Leu Tyr Ala Leu Asp Tyr
1               5


<210> SEQ ID NO 20
<211> LENGTH: 11
<212> TYPE: PRT
<213> ORGANISM: Murine

<400> SEQUENCE: 20

Lys Ala Ser Gln Asn Val Asp Thr Asn Val Ala
1               5                   10


<210> SEQ ID NO 21
<211> LENGTH: 7
<212> TYPE: PRT
<213> ORGANISM: Murine

<400> SEQUENCE: 21

Ser Ala Ser Tyr Arg Tyr Ser
1               5


<210> SEQ ID NO 22
<211> LENGTH: 9
<212> TYPE: PRT
<213> ORGANISM: Murine

<400> SEQUENCE: 22
```

Gln Gln Tyr Asn Ser Asn Pro Leu Thr
1 5

<210> SEQ ID NO 23
<211> LENGTH: 6
<212> TYPE: PRT
<213> ORGANISM: Murine

<400> SEQUENCE: 23

Leu Tyr Ala Met Asn Phe
1 5

<210> SEQ ID NO 24
<211> LENGTH: 7
<212> TYPE: PRT
<213> ORGANISM: Murine

<400> SEQUENCE: 24

Ser Ala Ser Tyr Arg Phe Ser
1 5

<210> SEQ ID NO 25
<211> LENGTH: 6
<212> TYPE: PRT
<213> ORGANISM: Murine

<400> SEQUENCE: 25

Leu Tyr Ala Met Asp Tyr
1 5

<210> SEQ ID NO 26
<211> LENGTH: 6
<212> TYPE: PRT
<213> ORGANISM: Artificial sequence
<220> FEATURE:
<223> OTHER INFORMATION: HCDR3
<220> FEATURE:
<221> NAME/KEY: VARIANT
<222> LOCATION: (4)..(4)
<223> OTHER INFORMATION: Xaa can be L or M
<220> FEATURE:
<221> NAME/KEY: VARIANT
<222> LOCATION: (5)..(5)
<223> OTHER INFORMATION: Xaa can be D or N
<220> FEATURE:
<221> NAME/KEY: VARIANT
<222> LOCATION: (6)..(6)
<223> OTHER INFORMATION: Xaa can be Y or F

<400> SEQUENCE: 26

Leu Tyr Ala Xaa Xaa Xaa
1 5

<210> SEQ ID NO 27
<211> LENGTH: 7
<212> TYPE: PRT
<213> ORGANISM: Artificial sequence
<220> FEATURE:
<223> OTHER INFORMATION: LCDR2
<220> FEATURE:
<221> NAME/KEY: VARIANT
<222> LOCATION: (6)..(6)
<223> OTHER INFORMATION: Xaa can be Y or F

<400> SEQUENCE: 27

Ser Ala Ser Tyr Arg Xaa Ser
1 5

<210> SEQ ID NO 28
<211> LENGTH: 5
<212> TYPE: PRT
<213> ORGANISM: Murine

<400> SEQUENCE: 28

Arg Phe Ala Leu Ser
1               5

<210> SEQ ID NO 29
<211> LENGTH: 17
<212> TYPE: PRT
<213> ORGANISM: Murine

<400> SEQUENCE: 29

Ala Val Ser Arg Gly Gly Asp Tyr Thr Tyr Tyr Pro Asp Ser Met Lys
1               5                   10                  15

Gly

<210> SEQ ID NO 30
<211> LENGTH: 13
<212> TYPE: PRT
<213> ORGANISM: Murine

<400> SEQUENCE: 30

His Leu Tyr Gly Tyr Gly His Tyr Tyr Ala Met Asp Tyr
1               5                   10

<210> SEQ ID NO 31
<211> LENGTH: 11
<212> TYPE: PRT
<213> ORGANISM: Murine

<400> SEQUENCE: 31

Lys Ala Ser Gln Asp Val Asn Thr Ala Val Ala
1               5                   10

<210> SEQ ID NO 32
<211> LENGTH: 7
<212> TYPE: PRT
<213> ORGANISM: Murine

<400> SEQUENCE: 32

Ser Ala Ser Tyr Arg Tyr Thr
1               5

<210> SEQ ID NO 33
<211> LENGTH: 9
<212> TYPE: PRT
<213> ORGANISM: Murine

<400> SEQUENCE: 33

Gln Gln His Tyr Ser Thr Pro Tyr Thr
1               5

<210> SEQ ID NO 34
<211> LENGTH: 7
<212> TYPE: PRT
<213> ORGANISM: Murine

<400> SEQUENCE: 34

Ser Gly Glu Tyr Phe Trp Gly
1               5

<210> SEQ ID NO 35
<211> LENGTH: 16
<212> TYPE: PRT
<213> ORGANISM: Murine

<400> SEQUENCE: 35

Ser Ile Tyr Tyr Ser Gly Ser Thr Tyr Tyr Asn Pro Ser Leu Lys Ser
1 5 10 15

<210> SEQ ID NO 36
<211> LENGTH: 12
<212> TYPE: PRT
<213> ORGANISM: Murine

<400> SEQUENCE: 36

Ser Leu Lys Ala Ala Arg Arg Asp Ala Phe Asp Ile
1 5 10

<210> SEQ ID NO 37
<211> LENGTH: 11
<212> TYPE: PRT
<213> ORGANISM: Murine

<400> SEQUENCE: 37

Ser Gly His Lys Leu Gly Asp Lys Tyr Ala Tyr
1 5 10

<210> SEQ ID NO 38
<211> LENGTH: 7
<212> TYPE: PRT
<213> ORGANISM: Murine

<400> SEQUENCE: 38

Gln Asp Thr Lys Arg Pro Ser
1 5

<210> SEQ ID NO 39
<211> LENGTH: 9
<212> TYPE: PRT
<213> ORGANISM: Murine

<400> SEQUENCE: 39

Gln Thr Trp Asp Ser Ser Thr Gly Val
1 5

<210> SEQ ID NO 40
<211> LENGTH: 445
<212> TYPE: PRT
<213> ORGANISM: Artificial sequence
<220> FEATURE:
<223> OTHER INFORMATION: Heavy chain of OMS721

<400> SEQUENCE: 40

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Ser Arg Gly
20 25 30

Lys Met Gly Val Ser Trp Ile Arg Gln Pro Pro Gly Lys Ala Leu Glu
35 40 45

Trp Leu Ala His Ile Phe Ser Ser Asp Glu Lys Ser Tyr Arg Thr Ser
50 55 60

Leu Lys Ser Arg Leu Thr Ile Ser Lys Asp Thr Ser Lys Asn Gln Val
65 70 75 80

```
Val Leu Thr Met Thr Asn Met Asp Pro Val Asp Thr Ala Thr Tyr Tyr
                85                  90                  95

Cys Ala Arg Ile Arg Arg Gly Gly Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 41
<211> LENGTH: 212
<212> TYPE: PRT
<213> ORGANISM: Artificial sequence
<220> FEATURE:
<223> OTHER INFORMATION: Light chain of OMS721

<400> SEQUENCE: 41

Gln Pro Val Leu Thr Gln Pro Pro Ser Leu Ser Val Ser Pro Gly Gln
1 5 10 15

Thr Ala Ser Ile Thr Cys Ser Gly Glu Lys Leu Gly Asp Lys Tyr Ala
20 25 30

Tyr Trp Tyr Gln Gln Lys Pro Gly Gln Ser Pro Val Leu Val Met Tyr
35 40 45

Gln Asp Lys Gln Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Ser Thr Ala Val
85 90 95

Phe Gly Gly Gly Thr Lys Leu Thr Val Leu Gly Gln Pro Lys Ala Ala
100 105 110

Pro Ser Val Thr Leu Phe Pro Pro Ser Ser Glu Glu Leu Gln Ala Asn
115 120 125

Lys Ala Thr Leu Val Cys Leu Ile Ser Asp Phe Tyr Pro Gly Ala Val
130 135 140

Thr Val Ala Trp Lys Ala Asp Ser Ser Pro Val Lys Ala Gly Val Glu
145 150 155 160

Thr Thr Thr Pro Ser Lys Gln Ser Asn Asn Lys Tyr Ala Ala Ser Ser
165 170 175

Tyr Leu Ser Leu Thr Pro Glu Gln Trp Lys Ser His Arg Ser Tyr Ser
180 185 190

Cys Gln Val Thr His Glu Gly Ser Thr Val Glu Lys Thr Val Ala Pro
195 200 205

Thr Glu Cys Ser
210

<210> SEQ ID NO 42
<211> LENGTH: 122
<212> TYPE: PRT
<213> ORGANISM: Artificial sequence
<220> FEATURE:
<223> OTHER INFORMATION: 29C1 VH1

<400> SEQUENCE: 42

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Arg Phe
20 25 30

Ala Leu Ser Trp Val Arg Gln Ala Pro Gly Lys Gly Leu Glu Trp Val
35 40 45

Ser Ala Val Ser Arg Gly Gly Asp Tyr Thr Tyr Tyr Pro Asp Ser Met
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Leu Tyr Gly Tyr Gly His Tyr Tyr Ala Met Asp Tyr Trp
100 105 110

Gly Gln Gly Thr Thr Val Thr Val Ser Ser
115 120

<210> SEQ ID NO 43
<211> LENGTH: 122

<212> TYPE: PRT
<213> ORGANISM: Artificial sequence
<220> FEATURE:
<223> OTHER INFORMATION: 29C1 VH2

<400> SEQUENCE: 43

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Phe
            20                  25                  30

Ala Leu Ser Trp Val Arg Gln Ala Pro Gly Lys Gly Leu Glu Trp Val
        35                  40                  45

Ala Ala Val Ser Arg Gly Gly Asp Tyr Thr Tyr Tyr Pro Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Tyr Gly Tyr Gly His Tyr Tyr Ala Met Asp Tyr Trp
            100                 105                 110

Gly Gln Gly Thr Thr Val Thr Val Ser Ser
        115                 120
```

<210> SEQ ID NO 44
<211> LENGTH: 122
<212> TYPE: PRT
<213> ORGANISM: Artificial sequence
<220> FEATURE:
<223> OTHER INFORMATION: 29C1 VH3

<400> SEQUENCE: 44

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Phe
            20                  25                  30

Ala Leu Ser Trp Val Arg Gln Ala Pro Gly Lys Gly Leu Glu Trp Val
        35                  40                  45

Ala Ala Val Ser Arg Gly Gly Asp Tyr Thr Tyr Tyr Pro Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Tyr Gly Tyr Gly His Tyr Tyr Ala Met Asp Tyr Trp
            100                 105                 110

Gly Gln Gly Thr Thr Val Thr Val Ser Ser
        115                 120
```

<210> SEQ ID NO 45
<211> LENGTH: 107
<212> TYPE: PRT
<213> ORGANISM: Artificial sequence
<220> FEATURE:
<223> OTHER INFORMATION: 29C1 VL1

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
```

```
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
                85                  90                  95

Thr Phe Gly Gly Gly Thr Lys Val Glu Ile Lys
            100                 105


<210> SEQ ID NO 46
<211> LENGTH: 107
<212> TYPE: PRT
<213> ORGANISM: Artificial sequence
<220> FEATURE:
<223> OTHER INFORMATION: 29C1 VL2

<400> SEQUENCE: 46

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
                85                  90                  95

Thr Phe Gly Gly Gly Thr Lys Val Glu Ile Lys
            100                 105


<210> SEQ ID NO 47
<211> LENGTH: 115
<212> TYPE: PRT
<213> ORGANISM: Artificial sequence
<220> FEATURE:
<223> OTHER INFORMATION: 77H11 VH1

<400> SEQUENCE: 47

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Arg Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Val Leu Tyr Ala Leu Asp Tyr Trp Gly Gln Gly Thr Thr Val Thr
            100                 105                 110
```

```
Val Ser Ser
        115


<210> SEQ ID NO 48
<211> LENGTH: 115
<212> TYPE: PRT
<213> ORGANISM: Artificial sequence
<220> FEATURE:
<223> OTHER INFORMATION: 77H11 VH2

<400> SEQUENCE: 48

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Arg Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Val Leu Tyr Ala Leu Asp Tyr Trp Gly Gln Gly Thr Thr Val Thr
            100                 105                 110

Val Ser Ser
        115


<210> SEQ ID NO 49
<211> LENGTH: 115
<212> TYPE: PRT
<213> ORGANISM: Artificial sequence
<220> FEATURE:
<223> OTHER INFORMATION: 77H11 VH3

<400> SEQUENCE: 49

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Arg Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Val Leu Tyr Ala Leu Asp Tyr Trp Gly Gln Gly Thr Thr Val Thr
            100                 105                 110

Val Ser Ser
        115


<210> SEQ ID NO 50
<211> LENGTH: 115
<212> TYPE: PRT
<213> ORGANISM: Artificial sequence
<220> FEATURE:
<223> OTHER INFORMATION: 77H11 VH4
```

<400> SEQUENCE: 50

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Asn Lys Leu Glu Trp
        35                  40                  45

Met Gly Tyr Ile Ser Tyr Ser Gly Arg Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Val Leu Tyr Ala Leu Asp Tyr Trp Gly Gln Gly Thr Thr Val Thr
            100                 105                 110

Val Ser Ser
        115

<210> SEQ ID NO 51
<211> LENGTH: 107
<212> TYPE: PRT
<213> ORGANISM: Artificial sequence
<220> FEATURE:
<223> OTHER INFORMATION: 77H11 VL1

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Val Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Ser Asn Pro Leu
                85                  90                  95

Thr Phe Gly Gln Gly Thr Lys Leu Glu Ile Lys
            100                 105

<210> SEQ ID NO 52
<211> LENGTH: 107
<212> TYPE: PRT
<213> ORGANISM: Artificial sequence
<220> FEATURE:
<223> OTHER INFORMATION: 77H11 VL2

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Val Ala Glu Tyr Tyr Cys Gln Gln Tyr Asn Ser Asn Pro Leu
                85                  90                  95

Thr Phe Gly Gln Gly Thr Lys Leu Glu Ile Lys
            100                 105


<210> SEQ ID NO 53
<211> LENGTH: 327
<212> TYPE: PRT
<213> ORGANISM: Artificial sequence
<220> FEATURE:
<223> OTHER INFORMATION: Human IgG4 Fc

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly Lys
                325


<210> SEQ ID NO 54
<211> LENGTH: 449
<212> TYPE: PRT
<213> ORGANISM: Artificial sequence
<220> FEATURE:
<223> OTHER INFORMATION: Heavy chain of 29C1

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Phe
            20                  25                  30

Ala Leu Ser Trp Val Arg Gln Ala Pro Gly Lys Gly Leu Glu Trp Val
        35                  40                  45

Ser Ala Val Ser Arg Gly Gly Asp Tyr Thr Tyr Tyr Pro Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Tyr Gly Tyr Gly His Tyr Tyr Ala Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 55
<211> LENGTH: 214
<212> TYPE: PRT
<213> ORGANISM: Artificial sequence
<220> FEATURE:
<223> OTHER INFORMATION: Light chain of 29C1

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 56
<211> LENGTH: 442
<212> TYPE: PRT
<213> ORGANISM: Artificial sequence
<220> FEATURE:
<223> OTHER INFORMATION: Heavy chain of 77H11
```

<400> SEQUENCE: 56

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ser Tyr Ser Gly Arg Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Val Leu Tyr Ala Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
```

```
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440


<210> SEQ ID NO 57
<211> LENGTH: 214
<212> TYPE: PRT
<213> ORGANISM: Artificial sequence
<220> FEATURE:
<223> OTHER INFORMATION: Light chain of 77H11

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Val Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Ser Asn Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 58
<211> LENGTH: 449
<212> TYPE: PRT
<213> ORGANISM: Artificial sequence
<220> FEATURE:
<223> OTHER INFORMATION: Heavy chain of 11165

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Glu Tyr Phe Trp Gly Trp Ile Arg Gln Pro Pro Gly Lys Gly Leu Glu
        35                  40                  45
```

```
Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Leu Lys Ala Ala Arg Arg Asp Ala Phe Asp Ile Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 59

<211> LENGTH: 212
<212> TYPE: PRT
<213> ORGANISM: Artificial sequence
<220> FEATURE:
<223> OTHER INFORMATION: Light chain of 11165

<400> SEQUENCE: 59

Gln Ser Val Leu Thr Gln Pro Pro Ser Val Ser Val Ser Pro Gly Gln
1 5 10 15

Thr Ala Ser Ile Thr Cys Ser Gly His Lys Leu Gly Asp Lys Tyr Ala
20 25 30

Tyr Trp Tyr Gln Gln Lys Pro Gly Gln Ser Pro Val Leu Val Ile Tyr
35 40 45

Gln Asp Thr Lys Arg Pro Ser Gly Ile Pro Glu Arg Phe Ser Gly Phe
50 55 60

Asn Ser Gly Asn Thr Ala Thr Leu Thr Ile Ser Gly Thr Gln Ala Thr
65 70 75 80

Asp Glu Ala Asp Tyr Tyr Cys Gln Thr Trp Asp Ser Ser Thr Gly Val
85 90 95

Phe Gly Ala Gly Thr Lys Val Thr Val Leu Gly Gln Pro Lys Ala Asn
100 105 110

Pro Thr Val Thr Leu Phe Pro Pro Ser Ser Glu Glu Leu Gln Ala Asn
115 120 125

Lys Ala Thr Leu Val Cys Leu Ile Ser Asp Phe Tyr Pro Gly Ala Val
130 135 140

Thr Val Ala Trp Lys Ala Asp Gly Ser Pro Val Lys Ala Gly Val Glu
145 150 155 160

Thr Thr Lys Pro Ser Lys Gln Ser Asn Asn Lys Tyr Ala Ala Ser Ser
165 170 175

Tyr Leu Ser Leu Thr Pro Glu Gln Trp Lys Ser His Arg Ser Tyr Ser
180 185 190

Cys Gln Val Thr His Glu Gly Ser Thr Val Glu Lys Thr Val Ala Pro
195 200 205

Thr Glu Cys Ser
210

<210> SEQ ID NO 60
<211> LENGTH: 15
<212> TYPE: PRT
<213> ORGANISM: Artificial sequence
<220> FEATURE:
<223> OTHER INFORMATION: Signal peptide

<400> SEQUENCE: 60

Met Arg Leu Leu Thr Leu Leu Gly Leu Leu Cys Gly Ser Val Ala
1 5 10 15

<210> SEQ ID NO 61
<211> LENGTH: 19
<212> TYPE: PRT
<213> ORGANISM: Artificial sequence
<220> FEATURE:
<223> OTHER INFORMATION: Signal peptide

<400> SEQUENCE: 61

Met Glu Phe Gly Leu Ser Trp Leu Phe Leu Val Ala Ile Leu Lys Gly
1 5 10 15

Val Gln Cys